(12) United States Patent
Altrogge et al.

(10) Patent No.: US 7,148,018 B2
(45) Date of Patent: Dec. 12, 2006

(54) PROTEASE-ACTIVATED RECEPTOR (PAR) MODULATOR ASSAYS

(75) Inventors: Ludger Altrogge, Pulheim (DE); Denis Monard, Füllinsdorf (CH)

(73) Assignee: Novartis Forschungsstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 379 days.

(21) Appl. No.: 10/149,623

(22) PCT Filed: Dec. 13, 2000

(86) PCT No.: PCT/EP00/12673

§ 371 (c)(1),
(2), (4) Date: Oct. 9, 2002

(87) PCT Pub. No.: WO01/44496

PCT Pub. Date: Jun. 21, 2001

(65) Prior Publication Data

US 2003/0148921 A1    Aug. 7, 2003

(30) Foreign Application Priority Data

Dec. 15, 1999 (GB) ............................. 9929674.1

(51) Int. Cl.
*G01N 33/53* (2006.01)
(52) U.S. Cl. .............. 435/7.1; 435/975; 435/7.72; 435/7.8; 435/7.9; 435/8
(58) Field of Classification Search ............. 435/7.1, 435/7.2
See application file for complete search history.

(56) References Cited

U.S. PATENT DOCUMENTS 5,605,809 A   2/1997  Komoriya et al.

FOREIGN PATENT DOCUMENTS

| EP | 518 557 | 12/1992 |
|----|---------|---------|
| WO | WO 91/19000 | 12/1991 |
| WO | WO 98/16657 | 10/1997 |
| WO | WO 98/39471 | 3/1998 |
| WO | WO 98/18456 | 5/1998 |
| WO | WO 99/50415 | 10/1999 |

OTHER PUBLICATIONS

Altrogge LM, et al. Analytical Biochem. 277(1):33-45, 2000.*
Loew D, et al. Biochemistry. 39(35):10812-22, Sep. 5, 2000.*
Karp M et al. Biomolecular Engineering 16(1-4):101-104, 1999.*
Fox et al., Identification of Potential Activators of Proteinase-Activated Receptor-2, Febs Letts, vol. 417, pp. 267-269, (1997).
Ishihara et al., "Protease-Activated Receptor 3 Is a Second Thrombin Receptor in Humans", Nature, vol. 386, No. 6624, pp. 502-506 (1997).
Kahn et al., "Gene and Locus Structure and Chromosomal Localization of the Protease-Activated Receptor Gene Family", J. Biol. Chem., vol. 273, No. 36, pp. 23290-23296 (1998).
Cronan, "Biotination of Proteins *in Vivo*. A Post-Translational Modification to Label, Purify, and Study Proteins", J. Biol. Chem., vol. 265, No. 18, pp. 10327-10333 (1990).
Vu et al., "Molecular Cloning of a Functional Thrombin Receptor Reveals a Novelproteolytic Mechanism of Receptor Activation", Cell, vol. 64, pp. 1057-1068 (1991).
Altrogge et al., "An Assay for High-Sensitivity Detection of Thrombin Activity and Determination of Proteases Activating or Inactivating Proteease-Activated Receptors", Anal. Biochem., vol. 277, No. 1, pp. 33-45 (2000).
Böhm et al., "Molecular Cloning, Expression and Potential Functions of the Human Proteinase-Activated Receptor-2", Biochem. J., vol. 314, pp. 1009-1016 (1996).
Brass et al., "Communication, Structure and Function of the Human Platelet Thrombin Receptor", J. Biol. Chem., vol. 267, No. 20, pp. 13795-13798 (1992).
Cavanaugh et al., "Reciprocal Modulation of Astrocyte Stellation by Thrombin and Protease Nexin-1", J. Neurochem., vol. 54, No. 5, pp. 1735-1743 (1990).
Even-Ram et al., "Thrombin Receptor Overexpression in Malignant and Physiological Invasion Processes", Nature Med., vol. 4, No. 8, pp. 909-914 (1998).
Fox et al., "Identification of Potential Activators of Proteinase-Activated Receptor-2", FEBS Lett., vol. 417, pp. 267-269 (1997).
Gerszten et al., Specificity of the Thrombin Receptor for Agonist Peptide is Defined by Its Extracellular Surface, Nature, vol. 368, pp. 648-651 (1994).
Grabham et al., "Thrombin Receptor Activation Stimulates Astrocyte Proliferation and Reversal of Stellation by Distinct Pathways: Involvement of Tyrosine Phosphorylation", J. Neurochem., vol. 64, No. 2, pp. 583-591 (1995).
Gurwitz et al., "Thrombin Modulates and Reverses Neuroblastoma Neurite Outgrowth", Proc. Natl. Acad. Sci. USA, vol. 85, pp. 3440-3444 (1988).
Hoffman et al., "The Prolonged Presence of Glia-Derived Nexin, An Endogenous Protease Inhibitor, in the Hippocampus After Ischemia-Induced Delayed Neuronal Death", Neuroscience, vol. 49, No. 2, pp. 397-408 (1992).
Hung et al., "Thrombin-Induced Events in Non-Platelet Cells Are Mediated by the Unique Proteolytic Mechanism Established for the Cloned Platelet Thrombin Receptor", J. Cell Biol., vol. 116, No. 3, pp. 827-832 (1992).
Ishii et al., "Determinants of Thrombin Receptor Cleavage", J. Biol. Chem., vol. 270, No. 27, pp. 16435-16440 (1995).
Kahn et al., "A Dual Thrombin Receptor System for Platelet Activation", Nature, vol. 394, pp. 690-694 (1998).
Kaufmann et al., "Thrombin Receptor Activation Results in Calcium Signaling and Protein Kinase C-Dependent Stimulation of DNA Synthesis in HEp-2g Laryngeal Carcinoma Cells", Cancer, vol. 80, No. 11, pp. 2068-2074 (1997).

(Continued)

*Primary Examiner*—Robert S. Landsman
(74) *Attorney, Agent, or Firm*—Paul J. Paglierani

(57) ABSTRACT

There is provided a method of identifying a PAR cleaving molecule comprising the steps of: (a) providing an immobilized PAR cleavage peptide linked to a reporter molecule; (b) contacting the immobilized PAR cleavage peptide with a PAR cleaving molecule; and (c) detecting release of the reporter molecule.

16 Claims, 1 Drawing Sheet

OTHER PUBLICATIONS

Kaufmann et al., "Functional Thrombin Receptor PAR1 in Primary Cultures of Human Glioblastoma Cells", NeuroReport, vol. 9, No. 4, pp. 709-712 (1998).

Kaufmann et al, "Proteinase-Activated Receptor-2-Mediated Signaling and Inhibition of DNA Synthesis in Human Pancreatic Cancer Cells", Int. J. Pancreatol., vol. 24, No. 2, pp. 97-102 (1998).

Kong et al., "Luminal Trypsin May Regulate Enterocytes Through Proteinase-Activated Receptor-2", Proc. Natl. Acad. Sci. USA, vol. 94, pp. 8884-8889 (1997).

Loret et al., "Differential Phenotypic Expression Induced in Cultured Rat Astroblasts by Acidic Fibroblast Growth Factor, Epidermal Growth Factor, and Thrombin", J. Biol. Chem., vol. 264, No. 14, pp. 8319-8327 (1989).

Molino et al., "Proteolysis of the Human Platelet and Endothelial Cell Thrombin Receptor by Neutrophil-Derived Cathepsin G", J. Biol. Chem., vol. 270, No. 19, pp. 11168-11175 (1995).

Molino et al., "Interactions of Mast Cell Tryptase with Thrombin Receptors and PAR-2", J. Biol. Chem., vol. 272, No. 7, pp. 4043-4049 (1997).

Molino et al., "Endothelial Cell Thrombin Receptors and PAR-2", J. Biol. Chem., vol. 272, No. 17, pp. 11133-11141 (1997).

Nelson et al., "Thrombin and Its Inhibitors Regulate Morphological and Biochemical Differentiation of Astrocytes In Vitro", Dev. Brain Res., vol. 54, pp. 93-104 (1990).

Nierodzik et al., "Protease-Activated Receptor 1 (PAR-1) Is Required and Rate-Limiting for Thrombin-Enhanced Experimental Pulmonary Metastasis", Blood, vol. 92, No. 10, pp. 3694-3700 (1998).

Nitsch et al., "Short Communication. The Glia-Derived Protease Nexin 1 Persists For Over 1 Year in Rat Brain Areas Selectively Lesioned by Transient Global Ischaemia", Eur. J. Neurosci., vol. 5, pp. 292-297 (1993).

Nystedt et al., "Molecular Cloning of A Potential Proteinase Activated Receptor", Proc. Natl. Acad. Sci. USA, vol. 91, pp. 9208-9212 (1994).

Nystedt et al., "The Mouse Proteinase-Activated Receptor-2 cDNA and Gene", J. Biol. Chem., vol. 270, No. 11, pp. 5950-5955 (1995).

Parry et al., "Cleavage of the Thrombin Receptor: Identification of Potential Activators and Inactivators", Biochem. J., vol. 320, pp. 335-341 (1996).

Pindon et al., "Thrombin-Induced Reversal of Astrocyte Stellation is Mediated by Activation of Protein Kinase C β-1", Eur. J. Biochem., vol. 255, pp. 766-774 (1998).

Rasmussen et al., "cDNA Cloning and Expression of a Hamster α-Thrombin Receptor Coupled to $Ca^{2+}$ Mobilization", FEBS, vol. 288, No. 1,2 pp. 123-128 (1991), Renesto et al., "Specific Inhibition of Thrombin-Induced Cell Activation by the Neutrophil Proteinases Elastase, Cathepsin G, and Proteinase 3: Evidence for Distinct Cleavage Sites Within the Aminoterminal Domain of the Thrombin Receptor", Blood, vol. 89, No. 6, pp. 1944-1953 (1997).

Saifeddine et al., "Rat Proteinase-Activated Receptor-2 (PAR-2): cDNA Sequence and Activity of Receptor-Derived Peptides in Gastric and Vascular Tissue", Br. J. Pharmacol., vol. 118, pp. 521-530 (1996).

Scotti et al., "Re-Expression of Glia-Derived Nexin/Protease Nexin 1 Depends on Mode of Lesion-Induction or Terminal Degeneration: Observations After Excitotoxin or 6-Hydroxydopamine Lesions of Rat Substantia Nigra", J. Neurosci. Res., vol. 37, pp. 155-168 (1994).

Smirnova et al., "Thrombin and Its Precursor in Human Cerebrospinal Fluid", Thromb. Haemost., vol. 78, pp. 1473-1479 (1997).

Smith-Swintosky et al, "Protease Nexin-1 and Thrombin Modulate Neuronal $Ca^{2+}$ Homeostasis and Sensitivity to Glucose Deprivation-Induced Injury", J. Neurosci., vol. 15, No. 8, pp. 5840-5850 (1995).

Suidan et al., "Thrombin Causes Neurite Retraction in Neuronal Cells through Activation of Cell Surface Receptors", Neuron, vol. 8, pp. 363-375 (1992).

Suidan et al., "Granzyme A Released Upon Stimulation of Cytotoxic T Lymphocytes Activates the Thrombin Receptor on Neuronal Cells and Astrocytes", Proc. Natl. Acad. Sci. USA, vol. 91, pp. 8112-8116 (1994).

Suidan et al., "Astrocyte Spreading in Response to Thrombin and Lysophosphatidic Acid Is Dependent on the Rho GTPase", GLIA, vol. 21, pp. 244-252 (1997).

Vaughan et al., "Thrombin Receptor Activation Protects Neurons and Astrocytes from Cell Death Produced by Environmental Insults", J. Neurosci., vol. 15, No. 7, pp. 5389-5401 (1995).

Vu et al., "Molecular Cloning of a Functional Thrombin Receptor Reveals a Novel Proteolytic Mechanism of Receptor Activation", Cell, vol. 64, pp. 1057-1068 (1991).

Xu et al., "Cloning and Characterization of Human Protease-Activated Receptor 4", Proc. Natl. Acad. Sci. USA, vol. 95, pp. 6642-6646 (1998).

Zhong et al., "Molecular Cloning of the Rat Vascular Smooth Muscle Thrombin Receptor", J. Biol. Chem., vol. 267, No. 24, pp. 16975-16979 (1992).

Perraud et al., "Thrombin Is A Potent Mitogen For Rat Astroblasts But Not For Oligodendroblasts And Neuroblasts In Primary Culture", Int. J. Devl. Neuroscience, vol. 5, No. 3, pp. 181-188 (1987).

* cited by examiner

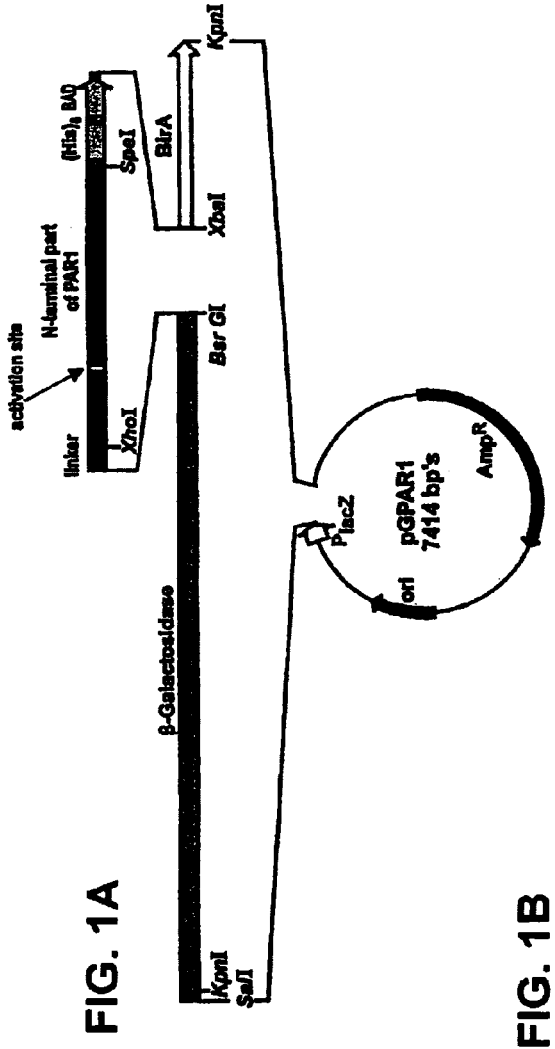

PROTEASE-ACTIVATED RECEPTOR (PAR) MODULATOR ASSAYS

This application is a 371 of PCT/EP0/12673 Dec. 13, 2000.

TECHNICAL FIELD

The present invention relates to assays for modulators of protease activated receptors, useful in the fields of thrombogenesis, neurobiology, oncology, osteoporosis and gut motility.

INTRODUCTION

The thrombin receptor (protease activated receptor-1, PAR1; Nystedt et al. (1994) *Proc Natl Acad Sci USA* 91, 9208–9212) is the prototypical member of a family of G-protein-coupled seven transmembrane domain receptors, named protease-activated receptors (PARs), now comprising four identified members in both mouse and human, some of which have also been identified in a number of other vertebrates (Nystedt et al. (1994); Nystedt et al. (1995) *J Biol Chem* 270, 5950–5955; Ishihara et al. (1997) *Nature* 386, 502–506; Kahn et al. (1998) *Nature* 394, 690–694; Vu et al. (1991) *Cell* 64, 1057–1068; Bohm et al. (1996) *Biochem J* 314 (Pt 3), 1009–1016; Xu et al. (1998) *Proc Natl Acad Sci USA* 95, 6642–6646; Rasmussen et al. (1991) *FEBS Lett* 288, 123–128; Zhong et al. (1992) *J Biol Chem* 267, 16975–16979; Saifeddine et al. (1996) *Br J Pharmacol* 118, 521–530; Gerszten et al. (1994) *Nature* 368, 648–651).

Thrombin cleaves human PAR1 after $Arg^{41}$, leading to a new N-terminus that intramolecularly triggers activation of the receptor (Vu et al., 1991). Similarly, other members of the PAR family are activated by protease cleavage. Activation of PAR1 can also be achieved by application of thrombin receptor activating peptides (TRAPs) that mimic the N-terminus generated by thrombin cleavage (Vu et al., 1991). PARs can thus be considered as peptide receptors carrying their own ligand that is unmasked upon proteolytic cleavage.

PARs have been implicated in various biological processes. Thrombin or TRAP treatment causes neurite retraction in cultured neuroblastoma cells (Gurwitz and Cunningham (1988) *Proc Natl Acad Sci USA* 85, 3440–3444; Suidan et al. (1992) *Neuron* 8, 363–375.) and reversal of stellation as well as proliferation of astrocytes (Cavanaugh et al. (1990) *J Neurochem* 54, 1735–1743; Grabham and Cunningham (1995) *J Neurochem* 64, 583–591; Loret et al. (1989) *J Biol Chem* 264, 8319–8327; Nelson and Siman (1990) *Brain Res Dev Brain Res* 54, 93–104; Pindon et al. (1998) *Eur J Biochem* 255, 766–774; Suidan et al. (1997) *Glia* 21, 244–25; Perraud et al. (1987) *Int J Dev Neurosci* 5, 181–188). Low amounts of thrombin increase survival of challenged hippocampal neurons and astrocytes but high doses of the protease cause neuronal apoptosis, suggesting a modulatory role for PAR1 in programmed cell death (Vaughan et al. (1995) *J Neurosci* 15, 5389–5401; Smith-Swintosky et al. (1995) *J Neurosci* 15, 5840–5850). Blocking PAR1 activation with an antibody directed against the newly created N-terminus antagonizes thrombin induced platelet activation (Hung et al. (1992) *J Cell Biol* 116, 827–832; Brass et al. (1992) *J Biol Chem* 267, 13795–13798) as well as the neurite retraction response of neuroblastoma cells (Suidan et al. (1994) *Proc Natl Acad Sci USA* 91, 8112–8116). PAR1 is highly expressed in human cancer cell lines and biopsies, indicating its involvement in mitogenic and metastatic behaviour of tumor cells (Even-Ram et al. (1998) *Nat Med* 4, 909–914; Kaufmann et al. (1997) *Cancer* 80, 2068–2074; Kaufmann et al. (1998a) *Neuroreport* 9, 709–712; Nierodzik et al. (1998) *Blood* 92, 3694–3700). While PAR1 activation stimulates DNA synthesis in Hep-2g cancer cells (Kaufmann, et al., 1997), PAR2 activation leads to a decrease in DNA synthesis in the human pancreatic tumor cells MIA PaCa-2 (Kaufmann et al. (1998b) *Int. J. Pancreatol.* 24, 97–102). PAR1 mediates activation of human platelets, while mice derived platelets are activated by PAR3 (Ishihara et al., 1997). Low levels of PAR4 have been detected as a second thrombin sensitive receptor in platelets (Kahn et al., 1998; Xu et al., 1998).

PAR1 can be cleaved and activated by thrombin, trypsin, plasmin, granzyme A and possibly also by activated protein C (Ishihara et al., 1997; Vu et al., 1991; Suidan et al., 1994; Parry et al. (1996) *Biochem J* 320, 335–341). In contrast, cleavage of PAR1 by cathepsin G, chymotrypsin, leukocyte elastase or myeloblastin (proteinase 3) removes the thrombin cleavage site, indicating a role for these proteases in inactivation of the receptor (Vu et al., 1991; Parry et al., 1996; Molino et al. (1995) *J Biol Chem* 270, 11168–11175; Renesto et al. (1997) *Blood* 89, 1944–1953), as cleavage at an alternate site produces a new N-terminal inactive in signal transduction. PAR2 differs from other known members of the PAR family, in that it contains a cleavage site susceptible to serine proteases such as trypsin, mast cell tryptase and acrosin (Nystedt et al. (1994); Molino et al. (1997a) *J Biol Chem* 272, 4043–4049; Fox et al. (1997) *FEBS Lett* 417, 267–269). The physiological activator of PAR2 in enterocytes is most likely trypsin (Kong et al. (1997) *Proc Natl Acad Sci USA* 94, 8884–8889), whereas in other tissues the activators of PAR2 are largely unknown.

In summary, detailed studies have been performed to identify proteases that are able to activate or inactivate PAR1 (Vu et al., 1991; Parry et al., 1996; Molino et al., 1995; Renesto et al., 1997; Ishii et al. (1995) *J Biol Chem* 270, 16435–16440); however little is known for PAR2 (Nystedt et al. (1994); Molino et al. (1997a); Fox et al. (1997); Molino et al. (1997b) *J Biol Chem* 272, 11133–11141), PAR3 (Ishihara et al., 1997) or PAR4 (Kahn et al., 1998; Xu et al., 1998).

PAR cleavage and activation assays have previously relied on the analysis of purified cleavage products resulting from the action of proteases on soluble peptide substrates based on the PAR cleavage site (Ishii, K. (1995) J. Biol. Chem. 270:16435–16440) or on measuring $^{45}Ca^{2+}$ release triggered by protease activation of PARs microinjected into Xenopus oocytes (Vu et al., 1991). These methods are rather cumbersome, insensitive and are not particularly amenable to high-throughput methodologies. In addition, the $Ca^{2+}$ signalling assay does not rule out proteases affecting $Ca^{2+}$ signalling in a manner independent of PAR activation. Assays that allow the identification of PAR-cleaving proteases and the characterization of protease specificity are required to further delineate the important biological role of PARs.

SUMMARY OF THE INVENTION

According to the present invention, we provide a method of identifying a PAR cleaving molecule comprising the steps of: (a) providing an immobilized PAR cleavage peptide linked to a reporter molecule; (b) contacting the immobilized PAR cleavage peptide with a PAR cleaving molecule; and (c) detecting release of the reporter molecule. The reporter molecule preferably provides an amplifiable signal, such as is the case when the reporter molecule is a reporter enzyme. The method is useful in identifying activators and inactivators of PAR, as well as modulators of PAR activation. The present invention also provides kits comprising a PAR fusion protein for use in the methods of the invention.

BRIEF DESCRIPTION OF THE DRAWINGS

FIG. 1A–B. A Schematic drawing of a plasmid for the production of a biotinylated GPAR1 fusion protein in E. coli. BAD, biotin acceptor domain; BirA, biotin holoenzyme synthetase. B C-terminal ends of the GPAR fusion proteins (GPAR1 is shown as SEQ ID NO:15; GPAR2 as SEQ ID NO:16; GPAR3 as SEQ ID NO:17; GPAR4 as SEQ ID:18). Small lettering, linkers; capital lettering, PAR extracellular N-terminal domain fragments; italic lettering, affinity tags; bold lettering and arrow, activation site residue.

DETAILED DESCRIPTION OF THE INVENTION

A sensitive method for the detection of proteases that are able to cleave protease-activated receptors (PARs) is provided. The assays allow detection of proteases cleaving the extracellular domains of PARs in minute amounts of biological samples, a quite relevant advantage for clinical assays. The assays can also be used for screening purposes, and allows the practitioner to detect and characterize protease activities present in low amounts, but nevertheless biologically relevant concentrations for the biological effects mediated by PARs. In addition, a more natural protease substrate can be designed than those previously used for PAR cleavage assays. Thus, the method is useful for the analysis of the proteolytic regulation of PARs and to screen for PAR modulators.

In one aspect of the invention, a method of detecting a PAR cleaving molecule is provided, the method comprising the steps of:
(a) providing an immobilized PAR cleavage peptide linked to a reporter molecule;
(b) contacting the immobilized PAR cleavage peptide with a PAR cleaving molecule; and
(c) detecting the release of the reporter molecule.

As used herein, the term "protease-activated receptor" or "PAR" is used to encompass a eukaryotic cell surface protein that can be specifically activated by a protease and that can signal the appropriate cascade of biological events (e.g., phosphoinositide hydrolysis, $Ca^{2+}$ efflux or platelet aggregation). A PAR cleaving molecule can be any molecule capable of cleaving PAR, such as a site-specific protease whose function is to activate (or inactivate) a PAR in a biological system.

The term "PAR cleavage peptide" as used herein means a peptide or polypeptide comprising the PAR amino-terminal exodomain or a fragment thereof, and comprising the endogenous protease cleavage site that activates (or inactivates) PAR. For example, mouse PAR1 (SEQ ID NO:19) and human PAR1 (SEQ ID NO:20) is cleaved by thrombin after $Arg^{41}$. Three amino acids directly upstream (N-terminal to, in the natural sequence) of $Arg^{41}$ followed by Arg are minimally required to detect the presence of a protease activator of PAR1 (VNP, followed by Arg (residues 38 to 41 of EMBL Accession No. L03529) (SEQ ID NO:19)). Mouse PAR2 is cleaved after $Arg^{38}$ (SEQ ID NO:21). Three amino acids directly upstream of $Arg^{38}$ followed by Arg are minimally required to detect the presence of a protease activator of mouse PAR2 (5KG, followed by Arg (residues 35 to 38 of EMBL Accession No. Z48043) (SEQ ID NO:21)). Mouse PAR3 (SEQ ID NO:22) is cleaved after $Lys^{37}$. Three amino acids directly upstream of $Lys^{37}$ followed by Lys are minimally required to detect the presence of a protease activator of PAR3 (LTI, followed by Lys (residues 34 to 37 of EMBL Accession No. U92972) (SEQ ID NO:22)). Human PAR4 (SEQ ID NO:23) is cleaved after $Arg^{47}$. Three amino acids directly upstream of $Arg^{47}$ followed by Arg are minimally required to detect the presence of a protease activator of human PAR4 (PAP, followed by Arg (residues 44 to 47 of EMBL Accession No. AF055917) (SEQ ID NO:23)). Similarly, for other PARs and for the detection of protease inactivators, the four amino acids N-terminal to the cleavage site are minimally included in the PAR cleavage peptide for detection of a protease.

Typically, additional amino acids are included in the PAR cleavage peptide, in particular, sequences of the PAR extracellular domain downstream of the cleavage site. For example, for the detection of thrombin using thrombin-sensitive PARS, the inclusion of the "hirudin-like sequence", GDEee is preferred, where the "hirudin-like sequence" minimally comprises GDE, but typically includes additional acidic amino acid residues, in particular additional E residues. Thus, for detection of thrombin, the minimal PAR cleavage peptide may be linked directly or indirectly to the "hirudin-like sequence", where indirect linkage can be achieved using PAR sequences naturally occurring between the minimal PAR cleavage peptide and the "hirudin-like sequence", or using an unrelated linker sequence. Preferably, extracellular domain sequences downstream of the cleavage site are included in the PAR cleavage peptide, in particular when the assay is being used to detect inactivating proteases.

More preferably, amino acid sequences surrounding the cleavage site in the naturally occurring PAR are included in the PAR cleavage peptide, thus mimicking the natural protease substrate. For example, the mouse PAR1 (EMBL Accession No. L03529) (SEQ ID NO:19), mouse PAR2 (EMBL Accession No. Z48043) (SEQ ID NO:21), mouse PAR3 (EMBL Accession No. U92972) (SEQ ID NO:22) and human PAR4 (EMBL Accession No. AF055917) (SEQ ID NO:23) amino-terminal exodomain (extracellular domain) fragments used in the Examples below extend from amino acids 27 to 78, 26 to 78, 21 to 92, and 17 to 78, respectively (amino acid numbering corresponds to EMBL database numbering), thus allowing detection of PAR activators and inactivators.

Although the specific examples provided herein are limited to known PARs, it will be apparent to one of ordinary skill in the art that PARs yet to be identified, or fragments thereof, are easily prepared in light of the teachings of the present specification. For example, oligonucleotide templates for the PCR-amplification of the coding sequences for the extracellular domains of the different PARs can be modified for use according to the extent of homology between the known and new PARs and depending on hybridization conditions. Alternatively, if sufficient identity exists between the two sequences, the same template can be used without further modification. Alternatively, suitable pairs of oligonucleotide templates can be used. In addition, variants of the naturally occurring sequence is foreseen, in particular conservative substitutions of amino acids not essential for cleavage at the biological cleavage site.

In a further embodiment, it is advantageous to include a transmembrane domain in the PAR cleavage peptide. A transmembrane domain are hydrophobic regions that can be identified as such by computer-aided hydropathy plots. For example, the seven transmembrane domains of PAR1 are identified in this manner by Vu et al. (1991, see FIG. 5). The inclusion of a transmembrane domain in the PAR cleavage peptide is particularly useful for the detection of proteases upon expression of the PAR cleavage peptide on a cell's surface, the transmembrane domain allowing anchorage of the peptide to the cell's membrane. The transmembrane domain can be of any origin although the inclusion of a PAR transmembrane domain is preferred. For ease of preparation, the PAR exodomain followed by its first transmembrane domain would typically be used in this embodiment (e.g., including amino acids 99–127 of PAR 1 (Vu et al. (1991).

The PAR cleavage peptide is linked to a reporter molecule. The reporter molecule (i.e., a signal generating molecule) can be any molecule capable of providing a detectable change. Such reporter molecules include fluorescent moieties (e.g., fluorescent proteins or chemical fluorescent labels), radioactive moieties, phosphorescent moieties, antigens, reporter enzymes and the like. Preferably, the reporter molecule is a reporter enzyme whose activity brings about a detectable change. Such reporter enzymes include, but are not limited to, the following: beta-galactosidase, glucosidases, chloramphenicol acetyltransferase (CAT), glucoronidases, luciferase, peroxidases, phosphatases, oxidoreductases, dehydrogenases, transferases, isomerases, kinases, reductases, deaminases, catalases and urease.

In selecting a reporter molecule to be used in the presently claimed method, it is imperative that the reporter molecule is not subject to inactivation by any agent in the sample, including inactivation by any protease activity present in a sample. The selection of an appropriate reporter molecule will be readily apparent to those skilled in the art. Presently preferred reporter molecules are reporter enzymes, such as beta-galactosidase, as exemplified in Example 1 below.

In another aspect of the invention, a PAR cleavage peptide is provided linked to a pair of interacting reporter molecules. Upon cleavage of the PAR cleavage peptide, one reporter is released from the PAR cleavage peptide, effecting a detectable change in the second reporter molecule. For example, a fusion protein can be designed comprising in N-terminal to C-terminal order: a first fluorescent protein (e.g., cyan fluorescent protein, CFP; yellow fluorescent protein, YFP; blue fluorescent protein, BFP; green fluorescent protein, GFP; all available commercially, Clontech Living Colors User Manual), a PAR cleavage peptide, and a second fluorescent protein. Immobilization of the PAR cleavage peptide can be achieved as described below. Upon cleavage at the PAR cleavage site, a measurable change in the fluorescence wavelength of the second reporter molecule occurs.

Preferred embodiments of this aspect of the invention comprise in N-terminal to C-terminal order, cyan fluorescent protein, PAR cleavage peptide, yellow fluorescent protein and an immobilizing tag (e.g., a biotin tag or a transmembrane domain); or yellow fluorescent protein, PAR cleavage peptide, red fluorescent protein and an immobilizing tag (e.g., a biotin tag or a transmembrane domain). It will be apparent to those in the art that other interacting reporter molecules can be used, for example Aequorin and GFP, luciferase and YFP. Preferably, the two interacting reporter molecules are separated by at least 15 amino acids, more preferably at least 20 amino acids, most preferably at least 30 amino acids, thus mimicking the naturally occurring PAR sequences.

Linkage of the reporter molecule to the PAR cleavage peptide can be achieved by any means known in the art (or means yet to be discovered) provided that (i) the PAR cleavage peptide can be recognized by its protease, and (ii) upon protease action on the PAR cleavage peptide, a reporter molecule is released in a detectable manner. Thus, linkage can be achieved by chemical reaction, by incorporation of a reporter molecule during synthesis of the PAR cleavage peptide, or by contiguous synthesis. For example, when the reporter molecule is a protein, a fusion protein comprising the reporter molecule, the PAR cleavage peptide and other optional sequences can be easily prepared by recombinant or chemical methods.

In brief, the DNA coding for the fusion protein may be comprised in a nucleic acid expression cassette comprising a promoter operably linked to the nucleic acid encoding the fusion protein and optionally to transcription termination signals. The fused polypeptides of the fusion protein may be connected directly or by a spacer. The PAR cleavage peptide can be N-terminal or C-terminal to the reporter molecule, depending on the particular design of the assay (see below).

The promoter can be of almost any origin. It is for example possible to use a tightly regulated promoter or the promoter that is naturally adjacent to a PAR gene. Preferred are promoters that are active in the chosen host cells like the SV40, tac, beta-actin, metallothionein, T7, polyhedrin and cytomegalovirus promoter. A particularly preferred promoter is the lacZ promoter, as exemplified in Example 1, below. Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII geneor the acid phosphatase (PH05) gene can be used.

A DNA sequence containing the transcription termination signals is preferably the 3' flanking sequence of a gene that contains proper signals for transcription termination and polyadenylation for the desired host. Suitable signals are, for example, the polyadenylation signal of the human growth hormone, of the DHFR gene and of the rabbit beta-globin gene.

In some embodiments, where anchorage to a cell membrane is not desired, it is also possible to use a polypeptide expression cassette additionally containing a signal sequence that causes the protein to be secreted into the medium. Suitable signal sequences are known in the art. Accordingly, in these kinds of expression cassettes a promoter is operably linked to a first DNA sequence encoding a signal peptide linked in the proper reading frame to a second DNA sequence coding for the fusion protein, and a DNA sequence containing transcription termination signals.

The promoter, the DNA sequence coding for the fusion protein and the DNA sequence containing transcription termination signals are operably linked to each other, i.e., they are juxtaposed in such a manner that their normal functions are maintained. The array is such that the promoter effects proper expression of the structural gene and the transcription termination signals effect proper termination of transcription and polyadenylation.

The expression cassettes for synthesis of the fusion protein may be inserted into the desired host in form of a stable plasmid or directly into the chromosome, of which the latter is preferred.

It is likewise possible that the expression plasmids include one or more, especially one or two, selective genetic markers for the host used for the construction, amplification and test of the plasmid, such as a marker and an origin of replication for a bacterial host, especially *Escherichia coli*.

As to the selective gene markers, any marker gene can be used which facilitates the selection for transformants due to the phenotypic expression of the marker gene. Suitable markers are, for example, those expressing antibiotic resistance or, in the case of auxotrophic host mutants, genes which complement host lesions. Corresponding genes confer, for example, resistance to the antibiotics tetracycline, ampicillin, G418, hygromycin, kanamycin, chloramphenicol, carbenicillin, zeocin, blasticydin or bleomycin, or provide for prototrophy in an auxotrophic mutant, for example the URA3, LEU2, LYS2, HIS3 or TRP1 gene.

As the amplification of the expression plasmids is usually done in a prokaryote, such as E. coli, a replication origin is included advantageously. This can be obtained from corresponding prokaryotic plasmids, for example E. coli plasmids, such as pBluescript® pBR322, pTZ18R, or a pUC plasmid, for example pUC18 or pUC19, which contain both prokaryotic, e.g. E. coli, replication origin and genetic marker conferring resistance to antibiotics, such as ampicillin and tetracycline.

Preferred nucleic acids coding for the fusion protein are described in Examples 1–5 below.

The expression plasmids are prepared by methods known in the art, for example by linking the polypeptide expression cassette, the DNA fragments containing selective genetic markers for the host, and the origin(s) of replication in the predetermined order using conventional chemical or biological in vitro synthesis procedures. Preferably, the plasmids are constructed and prepared using recombinant DNA techniques. For the preparation by recombinant DNA techniques suitable DNA fragments are ligated in vitro in conventional manner. The ligation mixture is then transformed into a suitable prokaryotic or eukaryotic host depending on the nature of the regulatory elements used, and a transformant containing the desired vector is selected according to conventional procedures. The plasmids can be multiplicated by means of the transformed hosts and can be isolated in conventional manner. The choice of the host depends on the regulatory sequences located on the vector. For the construction and multiplication of the vector a prokaryotic host, e.g. E. coli, is preferred.

A suitable host for the production of the fusion protein is a eukaryotic or prokaryotic cell, for example a mammalian, nematode, insect, yeast or bacterial cell. The suitable host can be transfected by the standard methods in genetic engineering, for example with the aid of a virus, lipid vesicles, particle gun or electroporation. To increase the amount of protein produced, it is advantageous to use a high copy plasmid or the plasmid DNA is integrated into the genome in several copies. The latter can be achieved, for example, through applying a selective stress, e.g., using methotrexate. The transfected host cells can be cultured by standard methods in cell culture.

Proteins may also be obtained by synthetic means rather than derived from natural sources, using commercially available protein synthesisers or even ordered from a commercial peptide synthesis service. Synthesized proteins may comprise any desired sequence modifications, including the use of altered amino acid residues or the addition of heterologous groups or side-chains to the polypeptide, and incorporation of labels or tags.

For use in the PAR cleavage assays of the present invention, the PAR cleavage peptide-reporter molecule is immobilized on a solid support. The solid support can be a multiwell plate, a gel, a matrix, a bead, a membrane or a tube, for example, and may be made of various materials, including without limitation, cellulose, agarose, dextran, polycarbonate, nylon, polyethylene, polycarbonates, and glass. In some embodiments, the solid support can be a membrane or surface, such as provided by a liposome or a cell.

The PAR cleavage peptide-reporter molecule is immobilized on a solid support in a manner such that a reporter molecule is released upon action of the protease if the enzymatically active protease is present in the sample. Immobilization can be achieved by any manner provided that the PAR cleavage site is accessible to its protease. Thus, an oriented attachment of the PAR cleavage peptide is typically required. Such oriented attachment can be achieved by various methods known in the art, including specific chemical reaction of the terminal end of the protein to reactive groups on the support, the attachment of a tag to the terminal end of the protein which can be captured by a receptor that specifically binds the tag (e.g., biotin-streptavidin, biotin-avidin, antibody-epitope interactions could be used as receptor-tag pairs) or any other manner that will be apparent to the artisan. Although the PAR cleavage peptide can be N-terminal or C-terminal to the reporter molecule, the PAR cleavage peptide will typically separate the tag (or other immobilizing means) from the reporter molecule to allow release of the reporter molecule upon action of the protease.

A preferred immobilizing means using biotin-streptavidin interactions is described in Example 1 below. Although this particular example illustrates the invention by incorporating biotin into the fusion protein, any method of incorporating such tags can be used, provided that the cleavage site is not masked or destroyed. This is important, not only for the presentation of the cleavage site to a protease, but also to allow separation of protease released reporter molecule from the immobilized PAR cleavage peptide-reporter molecule. Thus, non-specific chemical cross-linking of the PAR cleavage peptide-reporter molecule to a solid surface is not envisioned in the practice of the present invention.

In one aspect of the invention, the fusion protein is expressed on the surface of a cell and contains a transmembrane domain. The transmembrane domain expressed as part of the fusion protein can thus be envisioned as a "tag" immobilizing the fusion protein to the cell surface. A reporter molecule is provided N-terminal to the PAR cleavage peptide to allow release and subsequent detection of the reporter molecule upon protease action.

The immobilized PAR cleavage peptide-reporter molecule is contacted with a PAR cleaving molecule (or protease). The protease can be a known protease, which can be commercially available, or present in a biological sample, for example. The protease can also be provided in the form of a library of proteins, and the assay of the invention is then used to detect and isolate, or otherwise identify, the protease.

Protease samples may be obtained, for example, by extraction from a natural source, by expression of a recombinant nucleic acid encoding a protease, or by chemically synthesizing the protease. Numerous tumor cell lines (e.g., melanoma, breast carcinoma and neuroblastoma cell lines, available from the ATCC) are known to release known and non-characterized proteases, which can be used as a source of protease. In addition, tissues known to have activated PARs (and therefore biologically relevant protease) can be used, such as brain sections, reproductive tissue sections or gut tissue sections. Alternatively, body fluids, such as cerebrospinal fluid, ascites, urine, serum or blood can be used as a source of protease.

Protease can be isolated from natural sources by conventional means, from tissues or from cultured cells. During the isolation conventional additives like protein stabilisers, specific inhibitors of proteinases and the like may be added. For example, when the polypeptide is isolated from tissue culture, the first step consists usually in lysing the cells or, in the case where the polypeptide is secreted into the medium, in separating the cells from the culture fluid, typically by means of centrifugation. In the presence of additional proteins and impurities, the resulting supernatant can be enriched for the protease by removing most of the non-proteinaceous material, and precipitating proteins by saturating the solution with ammonium sulphate or the like. Contaminating proteins can also be precipitated by means of acidification with acetic acid and other conventional means. Other purification steps may include, for example, removing lectins, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, gel-permeation or ultrafiltration, by affinity chromatography, or by other processes, especially those known from the literature.

Purity of the protease can be measured by any appropriate method, e.g., column chromatography, polyacrylamide gel electrophoresis, or HPLC analysis. The protease is substantially pure if it can be isolated to a band in a gel.

Alternatively, various libraries of natural products can be tested for protease activity or indeed, expression libraries can be screened for released protease activity using the assays of the invention. For example, although single clones can be tested, for ease of handling, pools of clones from an expression library can be expressed in a suitable cell line, such as a cell line that is able to express, secrete and activate protease. By growing the cells in a suitable medium (e.g., serum-free medium, such as Dulbecco's Modified Eagle Medium (DMEM) or RPMI 1640 medium, optionally replenished with trace elements and growth sustaining supplements) within a receptacle (e.g., 96-well plates), conditioned medium is produced (i.e., medium containing secreted factors from the cells) which can be then analyzed for protease activity using the methods described herein. Once a pool is identified as producing higher levels of protease activity, the cells can be diluted with medium, separated, grown and tested as described above until the clone expressing the protease is identified.

The protease sample, whether provided as a mixture of molecules, in isolated form, as a body fluid, cell extract, conditioned medium, cells or as a tissue sample, is contacted with the immobilized PAR cleavage peptide-reporter molecule to allow cleavage of the PAR cleavage peptide, thereby releasing the reporter molecule. The release of the reporter molecule is then detected and indicates the presence of a PAR cleaving molecule in the sample.

Because the reporter molecule linked to the PAR cleavage peptide can interfere with the detection of the released reporter molecule, the released reporter molecule will typically be separated from the PAR cleavage peptide-reporter molecule prior to detection. This is easily achieved when the PAR cleavage peptide-reporter molecule is immobilized to allow release of the reporter molecule into the surrounding medium upon incubation with the protease sample. Thus, after cleavage by a protease, the medium can be withdrawn and the presence of released reporter in the medium determined. Alternatively, if the PAR cleavage peptide-reporter molecule is immobilized on a removable support, the immobilized PAR-cleavage peptide-reporter molecule is removed leaving the medium in a suitable receptacle for further analysis.

The release of the reporter molecule can be determined by detecting any measurable signal, such as a change in colour, fluorescence, luminescence or radiation events in the sample. When the reporter molecule is an enzyme, the sample (or medium that has contained the sample) is combined with an indicator. The indicator is any species that is susceptible to a detectable change (e.g., a pH change, colour change, fluorescence or luminescence change, or a substrate/enzyme that can be detected by a second indicator) upon action of the reporter enzyme. A detectable change in the indicator is an indication that the enzymatically active protease is present in the sample. Conversely, the lack of a detectable change in the indicator is an indication that the enzymatically active protease is absent from the sample. Typically, the "detectable change" is at least a 2-fold increase in signal over background (where control assays are performed in the absence of sample), preferably at least a 5-fold increase, more preferably at least a 10-fold increase in signal over that in a control assay.

As described above, the biological cleavage sites for PAR activating agents are known for human and mouse PAR-1 (following $Arg^{41}$), mouse PAR-2 (following $Arg^{38}$), mouse PAR-3 (following $Lys^{37}$) and human PAR-4 (following $Arg^{47}$). As used herein, the term "biological cleavage site" refers to the site cleaved in vivo that results in a biological response (e.g., $Ca^{2+}$ influx, neurite retraction, phosphoinositide hydrolysis, or platelet aggregation). Thus, upon identification of a PAR cleaving molecule, the PAR cleaving molecule can be identified as a potential PAR activator or potential PAR inactivator based on where the protease cleavage peptide is cleaved by the protease. PAR cleaving molecules that cleave the PAR cleavage peptide at a site other than the "biological cleavage site" are classified as potential PAR inactivators, whereas PAR cleaving molecules that cleave the PAR cleavage peptide at the "biological cleavage site" are classified as potential PAR activators.

The biological cleavage site can be easily determined as is apparent to the artisan. The examples below describe the use of mutated PAR cleavage peptides where the biological cleavage site is altered so that cleavage at this site is disrupted. Any cleavage of the mutated PAR cleavage peptide is therefore at an alternate site to the "biological cleavage site" indicating the presence of an inactivator. Alternatively, the released reporter-cleaved (poly)peptide moiety, or preferably the immobilized cleaved PAR sequences can be sequenced, or an antibody specific for the cleavage site can be used to determine whether cleavage is at the biological cleavage site or not.

Once the potential activator/inactivator is classified, further analysis can be carried out to confirm the classification. Such tests are known in the art and include neurite outgrowth assays, phosphoinositide hydrolysis assays, $Ca^{2+}$ efflux assays, and platelet aggregation assays.

In a further aspect of the invention, a method is provided for screening potential PAR modulators by contacting the immobilized PAR cleavage peptide with a PAR activator/inactivator and a potential PAR modulator, and determining a change in the amount of cleavage at the cleavage site as compared to when said PAR modulator is absent. PAR modulators can inhibit the action of an inactivator, thereby allowing PAR activation, or potentiate the action of an inactivator, thereby enhancing PAR inactivation. Conversely, PAR modulators can inhibit the action of an activator, thereby inhibiting PAR activation, or potentiate the action of an activator, thereby further improving PAR activation.

The presence of a PAR modulator is detected by a change in the amount of cleavage of the PAR cleavage peptide in the presence of the PAR modulator as compared to when absent. Preferably, the change in activity differs by 20% to that of the control level, more preferably by 50% to that of the control level, or more preferably by 90% or more to that of the control level. An increase in cleavage at the biological cleavage site reflects the presence of an agonist, whereas a decrease in cleavage at the biological cleavage site reflects the presence of an antagonist. An increase in cleavage at a site other than the biological cleavage site (in particular C-terminal to the biological cleavage site) also reflects the presence of an antagonist.

Thus, an agonist is a molecule that enhances PAR activation as characterized by cleavage at the biological cleavage site, relative to control assays in the absence of activator or candidate agonist. An antagonist is a molecule that reduces PAR activation relative to control assays in the absence of candidate antagonist either by (i) promoting cleavage at a site other than the biological cleavage or (ii) inhibiting cleavage at the biological cleavage site (for example, by binding to PAR and thereby blocking PAR activation, or by binding to a PAR activator).

Suitable agonists and antagonists can be obtained from the same sources as proteases, as described above. Alternatively, libraries of chemical compounds, peptides, antibodies or natural products, or combinatorial chemistry can be used as sources.

Once identified, the action of the agonists or antagonists can be confirmed by functional assays. In addition, the agonists or antagonists can potentially be used to obtain a desired pharmacologic and/or physiologic effect. The effect may be prophylactic in terms of completely or partially preventing a disease/condition or symptom thereof and/or may be therapeutic in terms of a partial or complete cure for a disease/condition and/or adverse effect attributable to the disease. "Treatment" as used herein covers any treatment of a disease in a mammal, particular a human, and includes:
(a) preventing the disease/condition or symptom from occurring in a subject which may be predisposed to the disease/condition or symptom but has not yet been diagnosed as having it;
(b) inhibiting the disease/condition or symptom, i.e., arresting its development; or
(c) relieving the disease/condition symptom, i.e., causing regression of the disease/condition.

For example, PAR1 activation has been implicated in providing a neuroprotective effect (Vaughan et al., 1995); PAR1 is highly expressed in cancer cell lines and biopsies, suggesting its involvement in mitogenic and metastatic behaviour of tumor cells; PAR1 has also been implicated in Alzheimer's disease; the expression of PN-1, a potent antagonist of PAR-1 activation is persistently upregulated in reactive astrocytes after ischemia and stroke, or certain types of neurotoxin induced lesions, (Hoffmann et al., 1992; Nitsch et al., 1993; Scotti et al., 1994); PAR-3 activation has been implicated in enhancing gut motility: all providing examples of possible target diseases or conditions.

In a further aspect of the invention, the PAR cleavage assay can be used in measuring the content of protease or protease inhibitory activity in clinical samples. Example 7 below demonstrates that the assay is sufficiently sensitive to detect for the first time the presence and amount of thrombin activity in the CSF of humans, both in healthy patients and after traumatic head injury, leading to an increased thrombin level in the majority of the cases. Similarly, CSF from patients or experimental animals after ischemia or stroke can be analyzed for their levels of thrombin or thrombin inhibitory activity. The level of protease or protease inhibitor activity in a clinical sample may therefore act as a diagnostic and/or prognostic indicator.

In yet a further aspect of the invention, a kit is provided comprising at least one of the materials disclosed herein, for example any one of a PAR cleavage peptide, a PAR fusion protein as described herein, such as PAR beta-galactosidase fusion protein, or nucleic acid encoding the same, in combination with instructions for use in the assay of the invention.

The examples below are provided solely for illustrative purposes and are not to be found limiting to the appended claims. All publications cited herein are incorporated by reference in their entirety as if incorporated individually.

EXAMPLES

Example 1

Detection of PAR-1 Cleaving Protease

This example describes the preparation of a galactosidase-PAR1 (GPAR1) as a recombinant protein obtained by fusion of β-galactosidase, the extracellular domain of PAR-1, a His$_6$-tag, and a biotin acceptor domain for in vivo biotinylation. Cleavage of the GPAR-1 fusion protein immobilized to streptavidin leads to the release of active soluble β-galactosidase that provides a means of monitoring proteases able to cleave the extracellular domain of PAR-1. Used as an immobilized substrate, the GPAR-1 fusion protein allows for the first time the detection of thrombin in the subpicomolar range.

Strains and Media

*E. coli* strain SCS110 (Stratagene, La Jolla, Calif., USA) was used for propagating recombinant plasmids. Recombinant GPAR-1 was expressed in either the *E. coli* strain M15[pREP4] (Qiagen), SCS110 or XL1-Blue MR (Stratagene). *E. coli* cells were grown in 2×YT medium, supplemented with 100 µg/ml ampicillin (Sambrook et al. (1989) Molecular Cloning. A Laboratory Manual, Cold Spring Harbor Laboratory Press, Cold Spring Harbor, N.Y.). The medium was further supplemented with 50 µM biotin (Tsao et al. (1996) *Gene* 169, 59–64) for the production of biotinylated recombinant GPAR-1.

Construction of GPAR-1 Expression Vector

The plasmid pGPAR1 was constructed by ligation of four fragments generated by PCR:
(i) a fragment encoding β-galactosidase,
(ii) a fragment encoding the PAR1 exodomain,
(iii) a fragment encoding affinity tags, and
(iv) a fragment encoding the BirA enzyme (biotin holoenzyme synthetase), which catalyses a biotin modification (Barker and Campbell (1981) *J. Mol. Biol.* 146, 451–467), all flanked by restriction sites.

The DNA fragment encoding β-galactosidase was amplified from pSV-β- Galactosidase (available commercially from Promega) using 5'-CACACAGCGGCCGCGTCGAC-GATGAGC GAAAAATACATCGTCACCT-3' (SEQ ID NO:1) and 5'-CACACTTAATTAATCTAGATTTGT ACAGTTTTTGACACCAGACCAACTGGTAA-3' (SEQ ID NO:2) as primers.

The fragment encoding the PAR1 exodomain was amplified from pBSmThR, which contains mouse PAR1 cDNA in pBluescript (Niclouet al. (1994) *Cell Mol Biol* 40, 421–428) using 5'-CACACACCATGGGGTCGACGATGAGCGT-GTACAGTGGAGGTTCAGGCGGATCAAGCCA GCCA-GAATCAGAGAGGAC-3' (SEQ ID NO:3) and 5'-GAGAGAACTAGTGGGGCTGGTCA GATATCCG-GAG-3' (SEQ ID NO:4) as primers.

The DNA fragment encoding the affinity tags and containing additional restriction sites to allow subcloning of the other PCR products was generated by PCR using a synthetic DNA oligonucleotide (5'-CACACACCATGGGACTC-GAGGAGGTACTAGTGGAGGTTCACACCAT CAT-CACCACCATGCAGCGGCTCTGAAC-GATATTTTCGAAGCTCAGAAAATCGAATGGCA CGAGTAGTCTAGACGTCCAGGTACCAGAGAG-3' (SEQ ID NO:5).

The BirA fragment was amplified directly from suspended SCS110 *E. coli* cells using 5'-CACACATCTAGATAAG-GATCCATGAAGGATAACACCGTGCCACTG-3' (SEQ ID NO:6) and 5'-CACACAGGTACCAAGCT-TATTTTTCTGCACTACGCAGGGAT-3' (SEQ ID NO:7) as primers. A colony of SCS110 cells was suspended in 50 μl of LB medium. Two μl of the cell suspension were used as a template in a 100 μl PCR reaction under standard conditions.

All PCR reactions were performed with Taq DNA polymerase, supplemented with 1/50 volume Pwo DNA polymerase, in a 100 μl reaction according to the manufacturer's recommendations. All manipulations with recombinant DNA were carried out following standard procedures (Pepper et al. (1993) *J Cell Biol* 122, 673–684) and according to the specifications of the manufacturers. The DNA sequences were verified by DNA sequencing.

In brief, a fragment of the multiple cloning site of pBluescript SK⁻ (available commercially from Stratagene) was removed by cleaving with ClaI and SstII, followed by treatment with T4 polymerase to create blunt ends, and then ligated to create pBS-CS. The PCR products (fragments (i) through (iv) above) were stepwise ligated into the KpnI and SalI sites of pBS-CS, yielding pGPAR1 (FIG. 1A). The resulting recombinant plasmid, pGPAR1, thus has a first open reading frame encoding β-galactosidase, C-terminally fused to the extracellular domain fragment of PAR1, a $His_6$-tag and a biotin acceptor domain (BAD). A second open reading frame, preceded by an internal ribosome entry site was introduced into the construct to produce the biotin holoenzyme synthetase (BirA enzyme) from the same mRNA (Tsao et al., (1996) *Gene* 169, 59–64).

Expression and Purification of GPAR1 in *E. coli*

SCS110 *E. coli* cells transformed with pGPAR1 formed blue colonies when plated on media containing isopropyl-β-D-thiogalactopyranoside (IPTG) and 5-bromo-4-chloro-3-indolyl-β-D-galactopyranoside (X-Gal), whereas cells transformed with pBS-CS gave white colonies due to the disrupted gene of the α-complementation fragment of β-galactosidase (Sambrook et al., 1989). 1 litre of 2×YT medium containing 100 μg/ml ampicillin and 50 μM biotin (Tsao et al. (1996)) was inoculated with recombinant *E. coli* cells, grown to an $OD_{600}$ of 0.7 and protein expression was induced with 0.4 g/l IPTG. After induction for at least 16 hours, cells were harvested by centrifugation at 5500 rpm for 30 min at 4° C. in a Beckman J-6B/P centrifuge with a JS-5.2 rotor, and resuspended in 80 ml 1× lysis buffer [50 mM sodium phosphate, pH 8.0, 300 mM NaCl, 0.2 mM $MgCl_2$, 10 mM imidazole, 30 mM β-mercaptoethanol], supplemented with 1 mg/ml aprotinin and 1 mg/ml phenylmethylsulfonyl fluoride (PMSF) as protease inhibitors. After french pressing, the suspension was cleared by centrifugation at 35000 g for 30 min at 4° C. in a Sorvall SS-34 rotor. GPAR1 was purified by means of the $His_6$ affinity tag using $Ni^{2+}$-NTA agarose (available commercially from Qiagen). The cell lysate, produced as described above, was incubated overnight with 2.5 ml $Ni^{2+}$-NTA agarose, at 4° C. with mild shaking. After packing into a suitable column (for example, BioRad Econocolumn, 1.5×15 cm, available from BioRad, Hercules, Calif., USA), the agarose was washed with 100 ml 1× lysis buffer, 100 ml EtOH wash buffer [10 mM Tris/HCl, pH 8.0, 60 mM NaCl, 0.2 mM $MgCl_2$, 10 mM imidazole, 30 mM β-mercaptoethanol, 30% Ethanol], followed by another 100 ml of lysis buffer without addition of protease inhibitors. The column was incubated for 30 min at 4° C. with 5 ml elution buffer [50 mM sodium phosphate, pH 8.0, 2.5 M NaCl, 0.5 M imidazole] before collecting eluted purified GPAR1 fusion protein. The eluate was dialysed against Tris/acetate buffer [50 mM Tris/acetate pH 7.3, 300 mM NaCl, 1 mM $MgCl_2$]. For long term storage an equal volume of 100% glycerol was added to the purified GPAR preparation and aliquots were stored at −80° C.

Analysis of Purified GPAR-1

Recombinant GPAR-1 was analysed by SDS-PAGE on 7.5% acrylamide gels (Laemmli (1970) *Nature* 227, 680–685). The GPAR1 protein was electrophoresed for 1 hour at 200 V together with appropriate molecular weight markers (e.g., Benchmark protein ladder molecular weight markers available from Life Technologies or protein molecular weight markers available from Amersham Pharmacia Biotech).

For immunoblot and detection of the biotin modification of GPAR1, electrophoresed proteins were transferred onto a nitrocellulose membrane (Towbin et al. (1979) *Proc. Natl. Acad. Sci. U.S.A.* 76, 4350–4354). After washing the membrane and blocking nonspecific protein binding with blocking buffer [phosphate-buffered saline (PBS),1% Triton X-100, 1% bovine serum albumin (BSA)], one membrane was probed with a rabbit polyclonal anti-β-galactosidase antibody (available commercially from 5 Prime_3 Prime, Boulder Colo., USA), followed by three washes with washing buffer [PBS, 1% Triton X-100] and incubation with an alkaline phosphatase labelled swine anti-rabbit antibody, diluted 1/200 in blocking buffer. The other membrane was probed with alkaline phosphatase-streptavidin conjugate, diluted 1/200 in blocking buffer. All incubations were for 1 hour at room temperature. After washing three times with washing buffer and once with alkaline phosphatase buffer [100 mM Tris/HCl, pH 8.0, 100 mM NaCl, 5 mM $MgCl_2$], color development was performed with nitroblue tetrazolium (NBT)/5-bromo-4-chloro-3-indolyl phosphate (BCIP) in alkaline phosphatase buffer [330 μg/ml NBT, 165 μg/ml BCIP] for five minutes.

Properties of Purified GPAR1 Protein

Purified GPAR1 appeared as two bands on SDS-PAGE under reducing conditions which was independent of the *E. coli* strain used. The upper band showed the expected apparent molecular mass of 136 kDa and its reactivity with streptavidin after blotting onto a nitrocellulose membrane indicated that it was biotinylated. The lower band showed an apparent molecular mass of 127 kDa and was not biotinylated. Both bands were immunopositive for β-galactosidase. The absence of biotinylation and the smaller apparent molecular weight of the second band suggested that it was a truncated form of the protein, devoid of the C-terminal part. This assumption was further substantiated by the fact that removing the C-terminal part of GPAR1 by thrombin treatment affected only the full length protein, leading to the appearance of only one band at 127 kDa on SDS-PAGE. The ratio of truncated to full length protein was consistently obtained.

Assay of β-Galactosidase Activity

Galactosidase activity was measured in order to quantitate the amount of GPAR-1 in a purified sample. A purified GPAR1 sample (25–75 µl) was added to each well of a 96-well microtiter plate. After addition of substrate solution [25 mM Tris/Acetate, pH 7.3, 150 mM NaCl, 0.5 mM MgSO$_4$, 2.5 mg/ml ONPG, final concentration] to a final volume of 200 µl, the increase in OD$_{405}$ was recorded at room temperature for 5 to 30 min and displayed as the reaction velocity. The amount of β-galactosidase which gave a change in optical density of 0.001 OD/min, was defined as 1 unit. The OD development was recorded using a THERMOmax microplate reader using SOFTmax (Molecular Devices, Sunnyvale, Calif., USA).

Calibration of the β-Galactosidase Color Reaction

In order to calibrate the assay and to establish the relationship between the reaction velocity and the concentration of β-galactosidase, 75 µl of a standard solution containing 35 ng/ml to 10 µg/ml β-galactosidase (commercially available from Roche Diagnostics, Rotkreuz, Switzerland) were measured under the above mentioned conditions and the OD$_{405}$ development was recorded for 30 min.

A dose-response curve with β-galactosidase indicated that 1 pmol of β-galactosidase was equivalent to 819 units, as defined above. One unit was thus equivalent to a concentration of 16.3 pM β-galactosidase in the sample. The reaction velocity as a function of the concentration of β-galactosidase was linear up to 1.2 OD$_{405}$/min, corresponding to 20 nM of β-galactosidase.

Immobilization of GPAR1

GPAR1 was immobilized on the surface of Streptavidin-coated paramagnetic particles (SA-PMP's available commercially from Promega, Madison, Wis., USA), as follows. 25 µl SA-PMPs in suspension were washed three times with 1 ml PBS. 250 units of GPAR1 were added in a total volume of 200 µl PBS and incubated at room temperature for 1 hour with constant shaking. After washing three times with 1 ml PBS, GPAR1/SA-PMPs were resuspended in 100 µl PBS and assayed for β-galactosidase activity by adding 100 µl substrate solution and incubating at room temperature for 2 min. The reaction was stopped by addition of 50 µl 0.5 M EDTA, pH 8, and the colored supernatant was separated from the particles. The extent of the color reaction was measured photometrically at 405 nm. About 95% of the purified β-galactosidase activity immobilized on SA-PMPs, whereas only about 20% of the total β-galactosidase activity expressed by the GPAR1 construct could be immobilized on SA-PMPs, probably because of the formation of a C-terminal truncation of GPAR1.

For the immobilization of GPAR1 on streptavidin-coated 96-well microtiter plates (available commercially from Labsystems, Helsinki, Finland), 125 units of GPAR1 were added per well in a total volume of 100 µl of PBS and the plates were kept at 4° C. for two to four days until used. After the immobilization, 75 µl of the solution was measured for β-galactosidase activity as described above, in order to determine the immobilization efficiency. The immobilization efficiencies were found to be consistently in the range of 70 to 75%, with immobilization efficiency being at its highest after two days of incubation at 4° C.

Human thrombin was previously prepared and characterized by Stone and Hofsteenge (1986, *Biochemistry* 25, 4622–4628). Microtiter plates with immobilized GPAR1 were washed quickly three times with PBS in order to remove any unbound GPAR1 protein. Protease samples (in triplicate) were immediately added in 100 µl of enzyme buffer [50 mM Tris/HCl, pH 8.0, 100 mM NaCl, 0.1% PEG 6000, 0.02% Tween 20]. For example, thrombin was added to the immobilized GPAR1 in concentrations ranging from 50 fM to 10 pM in 100 µl enzyme buffer. To ensure thrombin activity was being measured, identical control samples were included except for the addition of 5 pM hirudin or 5 pM PN-1.

The microtiter plates were incubated at 37° C. for 3 hours in a moist atmosphere to allow protease cleaveage of GPAR1, leading to a release of β-galactosidase into the medium. The sample medium (75 µl) was then transferred to a fresh plate and assayed for β-galactosidase activity as described above by measuring the optical density change for 15 min at 405 nm. The data were expressed as picomoles β-galactosidase released versus protease concentration and time in minutes. The sensitivity of immobilized GPAR1 to cleavage by different proteases was evaluated by calculation of the initial slopes obtained from the dose-response curves performed for each protease.

Under these conditions, 50 fM thrombin was detectable with a linear range up to 250 fM. The assay was saturated above 0.5 to 1 pM. The initial slope, as calculated from values within the first linear phase, showed that under these assay conditions, 2.6 moles β-galactosidase are released per minute per mole thrombin. In the presence of recombinant hirudin or rat protease nexin-1 ((Markwardt (1957) *Hoppe Seylers Z Physiol Chem* 308, 147–156; Baker et al. (1980) *Cell* 21, 37–45; PN-1; Sommer et al. (1989) *Gene* 85, 453–459), both potent inhibitors of thrombin, the signal of the GPAR1 assay was almost completely abolished, showing the strict dependence on the proteolytic activity of thrombin.

As a control to ensure that the different protease samples did not affect β-galactosidase activity (e.g., by destroying enzyme activity), 90 units of GPAR1 were incubated per well of a 96-well microtiter plate without streptavidin coating, with 100 µl of enzyme buffer containing the proteases at different concentrations. The control samples were tested for β-galactosidase activity in the same way as those samples assayed using streptavidin coated microtiter plates.

In summary, the assay for PAR cleaving molecules using the fusion protein GPAR1 is exquisitively sensitive, allowing detection of thrombin at concentrations as low as 50 fM, at least 10-fold more sensitive than previously used methods relying on the specific chromogenic substrate S2238 (Chromogenix, Mölndal, Sweden).

Example 2

Specificity of GPAR1 Assay and Identification of PAR1 Activators and Inactivators In order to show that the thrombin cleavage took place at its expected cleavage site, a mutant form of GPAR1 was generated, where an R$^{45}$S mutation prevents cleavage by trypsin-like serine proteases. The expression vectors for mutant GPAR1 were generated by excision of the PAR1 fragment from pGPAR1 (see Example 1) and replacement with a mutant PAR1 encoding DNA fragment. The mutant PAR1 construct carried a point mutation at the codon for the first amino acid residue of the activation site, leading to an incorporation of serine instead of arginine, thus rendering this site resistant to cleavage by trypsin-like serine proteases, including thrombin. The mutant PAR1 encoding fragment was prepared from pBSmThR using 5'-CTCATG-TACAGTGGAGGTTCAGGAGGCTCGAGC-CAGCCAGAA TCAGAGAGGACAGATGCTACGGT-GAACCCCAGCTCATTCTTTCTAAGGAATC-3' (SEQ ID NO:8) and 5'-GAGAGAACTAGTGGGGCTGGTCA-GATATCCGGAG-3' (SEQ ID NO:4) as primers. Exchanging the $Arg^{45}$ residue for serine gave rise to the activation site mutant fusion protein $GPAR1^{R45S}$.

Protease assays were carried out as described in Example 1, except both GPAR1 and the mutant GPAR ($GPAR1^{R45S}$) were used for comparative analysis. Incubation of human thrombin (Stone and Hofsteenge, 1986) with immobilized $GPAR1^{R45S}$ led to a dramatic reduction of the detected signal mutant demonstrating that thrombin does indeed cleave GPAR1 predominantly after $Arg^{45}$. More than 30000 times more thrombin was needed to elicit a response with $GPAR1^{R45S}$. The initial rate for the thrombin response decreased from 2.6 $mol_{\beta\text{-}galactosidase}/(mol_{thrombin}*min)$ to about 70 $nmol_{\beta\text{-}galactosidase}/(mol_{thrombin}*min)$ (Table 1). This signal was not due to a contaminating activity in the thrombin preparation, as it was absent in the presence of hirudin, a specific thrombin inhibitor. The lower cleavage rate of $GPAR1^{R45S}$ suggests the existence of a second cleavage site for thrombin in mouse PAR1, which is cleaved with lower efficiency. Human PAR1 is known to contain a second thrombin cleavage site located five residues C-terminally of the activation site (Vu et al. (1991); Parry et al. (1996)).

Protease Profile of GPAR1 and $GPAR1^{R45S}$

After showing that the GPAR1 assay reflects well the ability of thrombin to cleave and activate PAR1, we examined the effect of other proteases on GPAR1 and its activation site mutant $GPAR1^{R45S}$. The following additional proteases were assayed essentially as described above: bovine type II chymotrypsin (Sigma, St. Louis, Mo., USA), bovine activated protein C (ICN, Costa Mesa, Calif., USA), human plasmin, human high-molecular-mass urokinase and bovine trypsin (all available from Fluka, Buchs, Switzerland), human leukocyte elastase (Merck Darmstadt, Germany), and human single-chain tPA (Calbiochem La Jolla, Calif., USA).

In the cases of trypsin and plasmin, the maximum signal was even higher than for thrombin. With $GPAR1^{R45S}$ as a substrate, the dose-response curves for trypsin and plasmin were slightly shifted to the right compared to GPAR1 and the initial rates decreased (Table 1), indicating that cleavage at the PAR1 activation site is favored by these proteases. Thus, trypsin and plasmin were clearly detectable and their efficiency sensitive to mutation of the activation site (Table 1), thus confirming their ability to activate PAR1 (Ishihara et al. (1997); Vu et al. (1991); Parry et al. (1996)). None of the proteases tested turned out to be as potent as thrombin.

Chymotrypsin and elastase, proteases with preference for cleavage after hydrophobic residues, showed no preference for cleavage of GPAR1 over $GPAR1^{R45S}$, and therefore can be classified as potential inactivators of PAR1. Chymotrypsin and elastase were even more effective when incubated with immobilized $GPAR1^{R45S}$ (Table 1).

The two plasminogen activators tested were each unable to cleave GPAR1 at considerable rates and thus do not seem to be involved in PAR1 signalling or regulation (Table 1). Only at the highest urokinase concentration tested, was a marginal signal obtained.

Both thrombin and activated protein C have been reported to be activators of PAR1 (Parry et al. (1996)). Activated protein C was demonstrated by the present assay to cleave only GPAR1 and was almost inactive on immobilized $GPAR1^{R45S}$. The activity of activated protein C was approximately 1000 times less compared to thrombin. To test whether activity resulting from activated protein C was due to a contamination of the preparation with thrombin, activated protein C was assayed with immobilized GPAR1 in the presence of hirudin. In the presence of hirudin, the signal resulting from activated protein C was completely abolished (Table 1) and is thus most likely due to a thrombin contamination of the preparation (Table 1) (Parry et al. (1996)).

At higher concentrations, trypsin, plasmin, elastase and chymotrypsin cleaved GPAR1 and $GPAR1^{R45S}$ not only in the PAR1 domain, but also in the β-galactosidase domain, causing a decrease of the signal even below the background level. However, these proteases could be measured successfully at a lower concentration range demonstrating the broad application of the assays.

In order to evaluate at which concentrations the different proteases could influence the assay by destroying β-galactosidase activity, GPAR1 was incubated with these proteases without prior immobilization, and the remaining β-galactosidase activity measured as described above in Example 1. None of the examined proteases caused a decrease in β-galactosidase activity at concentrations below 100 pM. The initial slopes of the dose response curves derived from values below this critical concentration demonstrated that the destruction of β-galactosidase does not contribute to the data obtained with this assay format.

Thus, in summary, the assay is useful for the detection of specific thrombin site cleavage. The assay is also sufficiently sensitive to detect proteases other than thrombin and at cleavage sites other than the thrombin cleavage site, thereby allowing the detection and identification of potential PAR1 activators and inactivators. If thrombin activity needs to be specifically detected in a mixture of proteases, thrombin can be measured as the activity that can be specifically inhibited by hirudin.

Example 3

Identification of PAR-2 Activators and Inactivators

This example describes the preparation of a galactosidase-PAR2 (GPAR2) fusion protein and its use in assays designed to detect PAR2 activators and inactivators.

The expression vectors for GPAR-2 or $GPAR2^{R34S}$ were prepared by excision of the PAR1 fragment from pGPAR1 with XhoI and SpeI (see Example 1) and replacement of the excised fragment with a DNA fragment encoding the mouse PAR-2 extracellular domain or its activation site mutant. The mouse PAR2 exodomain coding sequence was prepared by PCR using the synthetic DNA oligonucleotides 5'-CACA-CATGTACAGTGGAGGTTCAGGCGGCT CGAGC-GAGAACCTTGCACCGGGACGCAACAA-CAGTAAAGGA<u>AGA</u>AGTCTTATTGGCAG ATTAGAAACCCAGCCTCCAATCACTG-3' (SEQ ID NO:9) AND 5'-CACACAACTAGTGACC GTGGT-CAGCTTCCCGGTGAGGATGGACGCA-GAGAACTCATCGATGGAAAAGCCTGGTT CTACCG-GAACCCCTTTCCCAGTGATTGGAGGCTGGGTT-3' (SEQ ID NO:10) as templates. The PAR2 activation site mutant was prepared in the same way but instead of the oligonucleotide SEQ ID NO: 9, a similar oligonucleotide where the underlined AGA was replaced with AGC was used. Annealing the appropriate two oligonucleotides complementary at their 3' ends yielded a partially double stranded template, which was used in a PCR reaction. All other techniques were performed as described in Example 1, above. The DNA sequence of the resulting clone was verified by DNA sequencing.

GPAR2 was expressed in *E. coli* strain SCS110 (Stratagene, La Jolla, Calif., USA) or M15[pREP4] (Qiagen). As with GPAR1, a truncated GPAR2 was also present in the purified fraction of GPAR2. The ratio of truncated to full length proteins was consistent with that obtained with GPAR1, as was the immobilization efficiency for practice of the assay. In cleavage assays carried out as described in Example 2 but using immobilized GPAR2 and GPAR2$^{R34S}$ fusion proteins, GPAR2 was demonstrated to be the preferential substrate for trypsin at an initial rate of 370 mmol$_{\beta\text{-}galactosidase}$/(mol$_{trypsin}$*min) (Table 1). In comparison, an initial rate of 97 mmol$_{\beta\text{-}galactosidase}$/(mol$_{trypsin}$*min) was detected for GPAR1 (Table 1). About 9 fold more trypsin was needed to cleave the activation site mutant GPAR2$^{R34S}$. Plasmin cleaved GPAR2 two times more efficiently than GPAR2$^{R34S}$, but only at a 560 fold lower rate than trypsin (Table 1). Chymotrypsin and elastase showed a minor preference for wildtype GPAR2 over GPAR2$^{R34S}$ (Table 1). Chymotrypsin and elastase cleaved GPAR2 at a lower rate than GPAR1. No signal was obtained with activated protein C, the tested plasminogen activators or thrombin (Table 1).

Example 4

Identification of PAR-3 Activators and Inactivators

This example describes the preparation of a galactosidase-PAR3 (GPAR3) and its use in assays designed to detect PAR3 activators and inactivators.

The expression vectors for GPAR-3 or GPAR3$^{K37S}$ were prepared by excision of the PAR1 fragment from pGPAR1 with XhoI and SpeI (see Example 3) and replacement of the excised fragment with a DNA fragment encoding the mouse PAR-3 extracellular domain or its activation site mutant. The mouse PAR3 exodomain coding sequence was prepared by PCR using the synthetic DNA oligonucleotides 5'-TGTA-CAGTGGAGGTTCAGGCGGCTCGA GCGGCATAAAT-GTTTCAGACAACTCAGCAAAGCCAACCT-TAACTATT<u>AAG</u>AGTTTTAATG GGGGTCCCCAAAATACCTTTGAAGAAT-TCCCACTTTCTGACATAGAGG-3' (SEQ ID NO:11) and 5'-ACTAGTACTTAAGGAACTTCTCAGG-TATCCTATGGTAGCATTATTCACGTGG AGAGT-TGAAATACTGTCCTCGGGACACTC-CGCTTTTATAGTTGTGGTGGCTCCTGTCCA GCCCTCTATGTCAGAAAGTGGGA-3' (SEQ ID NO: 12) as templates. The PAR3 activation site mutant was prepared in the same way but instead of the oligonucleotide SEQ ID NO:11, a similar oligonucleotide where the underlined AAG was replaced with TCG was used. All other techniques were performed as described in Example 3. As with GPAR1 and GPAR2, a truncated GPAR3 was also present in the purified fraction of GPAR3. The ratio of truncated to full length proteins was consistent with that obtained with GPAR1, as was the immobilization efficiency for practice of the assay.

Cleavage assays were carried out as described in Example 3 but using immobilized GPAR3 and GPAR3$^{K37S}$ fusion proteins. PAR3 is the main thrombin receptor in mouse platelets (Ishihara et al. (1997), Kahn et al. (1998) *Nature* 394, 690–694), and correspondingly the immobilized GPAR3 fusion protein is also efficiently cleaved by thrombin (Table 1). However the initial rate of 41 mmol$_{\beta\text{-}galactosidase}$/(mol$_{thrombin}$*min) is about six times lower than for GPAR1. The activation site mutant GPAR3$^{K37S}$ shows a rate for β-galactosidase release by thrombin of 3.4 mmol$_{\beta\text{-}galactosidase}$/(mol$_{thrombin}$*min), thus reflecting the presence of a second possible thrombin cleavage site, which is cleaved at a higher rate than the second thrombin cleavage site in PAR1 (Table 1). When trypsin was incubated with GPAR3 or GPAR3$^{K37S}$, only a minor preference for cleavage of GPAR3 was observed (Table 1). A stronger effect of the mutation in the activation site of GPAR3 was seen with plasmin, which was about 120 times less active than thrombin (Table 1). The tissue plasminogen activator showed only a very weak signal with GPAR3, which was reduced when using GPAR3$^{K37S}$, indicating a preferred cleavage at the K37-S38 bond (Table 1). The values for uPA were too low to detect a similar difference (Table 1). No preference for GPAR3 was found for chymotrypsin or elastase (Table 1). Activated protein C did not cleave GPAR3 nor GPAR3$^{K37S}$ to an appreciable extent in the presence of hirudin (Table 1).

Example 5

Identification of PAR-4 Activators and Inactivators

This example describes the preparation of a galactosidase-PAR4 (GPAR4) fusion protein and its use in assays designed to detect PAR4 activators and inactivators.

The expression vectors for GPAR-4 or GPAR3$^{K37S}$ were prepared by excision of the PAR1 fragment from pGPAR1 with XhoI and SpeI (see Example 3) and replacement of the excised fragment with a DNA fragment encoding the human PAR-4 extracellular domain fragment or its activation site mutant. The human PAR4 exodomain fragment coding sequence was prepared by PCR using the synthetic DNA oligonucleotides 5'-CACACACTCGAGCGGCGG CAC-CCAGACCCCCAGCGTCTACGAC-GAGAGCGGGAGCACCGGAGGTGGTGATGACAG CACGCCCTCAATCCTGCCTGCCCCC <u>CGC</u>GGCTACCCAGGC-3' (SEQ ID NO: 13) and 5'-TGT-GTGACTAGTCCTGGTGGGCACCCAGC-CCAGAAGCAGTGCCCGTGAGCTGTCCGGA AGCTC-CAGGGTGTCACTGTCATTGGCACAGACTTGG CCTGGGTAGCCGCGGGGGG-3' (SEQ ID NO: 14) as templates. The PAR4 activation site mutant was prepared synthetically and was similar to the PAR4 exodomain fragment but the CGC underlined in SEQ ID NO:13 was replaced by AGC. All other techniques were performed as described in Example 3. As with GPAR1, GPAR2 and GPAR3, a truncated GPAR4 was also present in the purified fraction of GPAR4. The ratio of truncated to full length proteins was consistent with that obtained with GPAR1.

Protease Profile for GPAR4 and GPAR4$^{R47S}$

GPAR4 and GPAR4$^{R47S}$ were also tested with the same set of proteases under the same conditions as for the other GPARs. GPAR4 was efficiently cleaved by trypsin with a rate of 15 mmol$_{\beta\text{-}galactosidase}$/(mol$_{trypsin}$*min) (Table 1). Compared to the highest cleavage rates observed with GPAR1, GPAR2 and GPAR3, the cleavage rate of GPAR4 was at least one order of magnitude lower (Table 1). Thrombin, which is a known activator of PAR4 (Kahn et al. (1998), Xu et al. (1998)), cleaved GPAR4 at a rate of 4.3 mmol$_{\beta\text{-}galactosidase}$/(mol$_{thrombin}$*min), which was still three orders of magnitude lower than with GPAR1 (Table 1). However, both trypsin and thrombin were clearly less effective when incubated with GPAR4$^{R47S}$, with thrombin displaying a higher degree of specificity (Table 1). Plasmin cleaved both GPAR4 and GPAR4$^{R47S}$ with low efficiency but also displayed a preference for cleavage at the activation site of PAR4. Chymotrypsin and elastase cleaved both substrates with no preference for the wildtype substrate. Both plasminogen activators, as well as activated protein C did not cleave GPAR4 or GPAR4$^{R47S}$ at considerable rates (Table 1). Compared to GPAR1, all tested proteases cleaved GPAR4 and GPAR4$^{R47S}$ at much lower rates (Table 1).

Example 6

Comparative Analysis of PAR Activators and Inactivators

In this example, the use of wild type and mutant extracellular PAR domains allows the analysis of the proteolytic regulation of the different identified members of the PAR family and also provides a new and highly sensitive tool to identify yet unknown PAR-cleaving proteases.

A comparative analysis for proteolytic cleavage of murine PAR1, PAR2, PAR3 and human PAR4 was performed, involving mutated and non-mutated GPAR fusion proteins. The assays were carried out essentially as described above but with the addition of various proteases.

Thrombin

Thrombin cleaved GPAR1 (2.6 mol$_{\beta\text{-}galactosidase}$/(mol$_{thrombin}$*min), GPAR3 (410 mmol$_{\beta\text{-}galactosidase}$/(mol$_{thrombin}$*min), and GPAR4 (4.3 mmol$_{\beta\text{-}galactosidase}$/(mol$_{thrombin}$*min), specifically at the proteolytic activation site, i.e., cleavage was compromised by mutation of the activation site (Table 1). In contrast, cleavage of GPAR2 could not be observed (Table 1).

Trypsin

Trypsin cleaved all receptor fusion proteins with little specificity for the activation site, except for a marked preference of trypsin for cleavage at the activation site of GPAR2 (Table 1). The mutant forms were cleaved less efficiently, indicating the potential of trypsin to activate all PARs. While six potential cleavage sites for trypsin can be found in the exodomain of PAR2, mutation of the activation site still led to a 9 fold reduction in the efficiency of tryptic cleavage of GPAR2. Mutating the activation site of the other GPAR fusion proteins did not lead to such a strong reduction in cleavage by trypsin, clearly showing that PAR2 is optimized for cleavage by trypsin at this site (Table 1).

Activated Protein C and Plasminogen Activators

Neither activated protein C (in the presence of hirudin) nor the plasminogen activators cleave any GPAR fusion protein at considerable rates.

Plasmin

Plasmin, the fibrinolytic protease generated from plasminogen by the action of the plasminogen activators, cleaved all non-mutated GPAR proteins at a rate still affected by mutation of the activation site, but at least ten times lower compared to trypsin (Table 1). The weak efficiency with which plasmin is able to cleave the thrombin sensitive PARs possibly allows it to play a role in modulating PAR1 mediated responses in platelets, which cannot replace activated PARs by synthesis and membrane insertion of new receptor molecules (Molino et al. (1997) *J Biol Chem* 272, 6011–6017). The weak ability of plasmin to cleave GPAR2 at the activation site is in contrast to findings of Fox et al. who, using a peptidyl chloromethane inhibitor based on the four residues upstream of the activation site of PAR2, found that both thrombin and plasmin are unlikely to be activators of PAR2 (Fox et al. (1997) *FEBS Lett* 417, 267–269.). However, that assay could only detect interactions mediated by the four residues upstream of the activation site, while our determination uses additional PAR2 N-terminal extracellular domain sequences, a more biologically relevant substrate.

Chymotrypsin and Elastase

We also examined the cleavage of our GPAR fusion proteins by elastase and chymotrypsin, two proteases that possess a preference for cleavage after hydrophobic residues. GPAR1 was cleaved well by both enzymes, and the mutant GPAR1$^{R45S}$ was cleaved with even higher efficiency, clearly demonstrating that both proteases recognize and cleave sites other than the activation site (Table 1). The enhanced cleavage of GPAR1$^{R45S}$ can be explained by the introduction of an additional cleavage site in creating the R$^{45}$S mutation. In the case of GPAR2 and GPAR2$^{R34S}$, elastase gave a signal about five times lower than with GPAR1 and lower still for the mutant form (Table 1). Also, chymotrypsin cleaved GPAR2 better than the mutant: the signal was about ten times lower than with GPAR1 and similar to that with GPAR3 and GPAR4 and their mutants (Table 1). The signals for elastase and chymotrypsin vary between below or around 10 mmol$_{\beta\text{-}galactosidase}$/(mol$_{protease}$*min) and above or around 100 mmol$_{\beta\text{-}galactosidase}$/(mol$_{protease}$*min), (Table 1). The lower cleavage rates probably reflect cleavage outside the PAR-domains. While inactivation of PAR2 by elastase cannot be excluded, our data indicate that PAR4 is not a substrate for this enzyme. Chymotrypsin cleaves GPAR1 at a rate (58 mmol$_{\beta\text{-}galactosidase}$/(mol$_{thrombin}$*min), which suggests chymotryptic inactivation of PAR1.

Example 7

Measurement of Active Thrombin in the Cerebrospinal Fluid from Patients after Severe Head Trauma The cerebrospinal fluid (CSF) is a liquid which surrounds neurons and glial cells in the nervous system. It is separated from the blood system by the blood brain barrier and its solute composition is well controlled and maintained to allow normal neuronal function. Head injuries can lead to a temporal disruption of the blood brain barrier, thus possibly leading to the influx of blood components, including thrombin, into the brain.

Thrombin has been described to affect both cell survival and cell death of neurons and astrocytes after glucose deprivation or oxidative stress (Smith-Swintosky et al., 1995; Vaughan et al., 1995; Pike et al., 1996). Thrombin addition to cultured neuroblastoma cells or neurons elicits a very fast withdrawal of neurites (Gurwitz and Cunningham, 1988; Grand et al., 1989; Baird and Raper, 1995). These thrombin effects occur at picomolar concentrations (Gurwitz and Cunningham, 1988).

In a previous study using the pNA-substrate S2238, no active thrombin was found in the CSF (Smirnova et al., 1997). However, using an assay of the present invention, we were able to measure thrombin in subpicomolar quantities and have successfully measured thrombin levels in the CSF.

Samples of human cerebrospinal fluids (CSFs) were obtained from the Kantonspital, Basel. The samples were obtained from patients with severe head trauma, one patient with a subarachnoid haemorrhage and diagnosed brain death, and one healthy subject. The samples were obtained between 3 hours and 17 days after the injury; for comparison, a sample of blood from one patient was also provided.

Measurement of the Blood Content

The amount of contaminating blood was determined by measuring the $OD_{405}$ of different dilutions of the samples before starting the GPAR assay. The slopes of the curves of $OD_{405}$ vs reciprocal dilution were determined and compared. The value for the blood sample was defined as 100%, while the value for the control CSF from the healthy subject was defined as 0%. A linear relationship between blood content and $OD_{405}$ values was assumed.

Measurement of the thrombin Concentration

CSF samples were serially diluted in enzyme buffer 1×$EB_T$ [50 mM Tris/HCl, pH 8.0, 100 mM NaCl, 0.1% PEG 6000, 0.02% Tween 20] with dilutions ranging from 1/2 to 1/30,000. After measurement of the blood content, the diluted samples were assayed for the presence of thrombin-like activity in triplicates under the conditions described in Example 1.

The slopes of the linear part of the dose-response curves were determined and compared to the slope for the thrombin standard, in order to express the data as the picomolar concentration of thrombin in the sample. Due to a strong intrinsic absorption at 405 nm in blood, the β-galactosidase substrate ONPG could not be used for the blood sample. Instead the alternative substrate Chlorophenolred-β-D-galactopyranoside (CPRG; available commercially from Roche Diagnostics, Rotkreuz, Switzerland) was used, which allows measurement of β-galactosidase activity at 590 nm, without the interference of the intrinsic absorption of blood. CPRG was used at the same concentration as ONPG. The thrombin standard was measured accordingly.

The thrombin concentration could be precisely determined in the CSF samples, as indicated by the reference dose-response curve for thrombin, included during the measurement of each set of three samples. In the normal CSF sample and in blood, very similar levels of thrombin were detected with a concentration of 25 and 29 pM, respectively. In the CSF samples from patients after a severe head trauma, frequently a substantially higher thrombin level was found, which in patient 1 was even 17 times higher than the normal level already at 4 hours after the injury, and still 5 times higher after 10 hours. In the other patients both an increase in the thrombin concentration over time was observed (patients 2, 4), as well as a decrease (patient 3). From the remaining patients only a single sample was available, thus not allowing a direct comparison. From all patients there was at least one sample that displayed an elevated thrombin level, except for the CSF from a patient taken two days after subarachnoid haemorrhage. In this case, the thrombin level was normal but the CSF sample showed the highest amount of blood contamination (~18%) (patient 6). There was no correlation between the amount of blood contamination in the CSF and the thrombin concentration. From an additional patient a larger series of CSF samples was available, which were taken between 20 and 280 hrs after a severe head injury. While in the first phase after the trauma the thrombin concentration was in the range of normal CSF, it suddenly increased strongly after 2 days up to a maximal level of 370 pM thrombin, which was reached at 6 days after the trauma. Even up to 12 days after the trauma a three fold increased level of thrombin was still measured. Fluctuations in the thrombin levels were readily apparent, even on a daily basis, such as a strong increase seen between days 2 and 3, and a decrease followed again by an increase between days 5 and 8. When the same assay was performed in the presence of hirudin, no β-galactosidase release was detectable, identifying the observed protease activity as thrombin.

In summary, we have measured the thrombin concentration in CSF with concentrations in normal blood or CSF in the range of 25 to 30 pM and in cases of CSF from patients after a severe head trauma at levels as high as 400 pM or more. In all cases where an increased thrombin level was measured, the thrombin concentration was at least 100 pM. The high sensitivity of the assay allows the measurement of minute quantities of thrombin in biological or clinical samples, including CSF. Thus, the assay facilitates studies to determine whether thrombin is a risk factor in traumatic head injury, to predict the outcome of the injury depending on thrombin levels, and to determine whether care should be taken in order to specifically block thrombin activities in the CSF.

Example 8

Measurement of Protease Activity and Protease Inhibitory Activity in Brain Homogenates of PN-1 Knockout Mice and Heterozygous or Wild Type Littermates The serine protease inhibitor PN-1 shows a distinct temporal and spatial expression pattern in the developing cartilage, lung, skin, urogenital tract and in the central and peripheral nervous system (Mansuy et al., 1993). The gene for PN-1 has been disrupted in mice in order to better define the suggested roles for PN-1 during development and adulthood (Lüthi et al. 1997). The present example demonstrates the measurement of the amounts of protease or protease inhibitory activity in brain homogenates obtained from PN-1 deficient mice and from heterozygous and wild type littermates using the substrate S2238 and the GPAR assay. We analysed 14 days old PN-1 knockout mice and littermates described earlier (Lüthi et al., 1997) which were back-crossed into the C57/Bl6 mouse line (commercially available).

Preparation of Brain Homogenates

Three mice from one litter of back-crossed PN-1 knock out mice were anaesthetized and perfused with sucrose buffer [10 mM HEPES, pH 7.5, 320 mM sucrose, 1 mM EDTA, 0.2% Tween 20]. The brains were then excised and homogenized for 45 seconds in sucrose buffer at a ratio of 2 ml per brain using a polytron homogenizer (Kinematica, Luzern, Switzerland). The cell debris was separated by centrifuging at 13,000 rpm in a Heraeus benchtop centrifuge at room temperature for 15 minutes. The supernatant was subsequently sterilized by filtering first through a 0.45 μm and then through a 0.22 μm Millipore filter. The homogenates were stored frozen at −80° C. until use.

Measurement of the Protease and Thrombin Inhibitory Activity.

The brain homogenate supernatants were serially diluted in enzyme buffer 1×$EB_T$ [50 mM Tris/HCl, pH 8.0, 100 mM NaCl, 0.1% PEG 6000, 0.02% Tween 20] with dilutions ranging from 1/100 to 1/10,000. The diluted samples were assayed for the presence of thrombin-like activity in triplicates under the conditions described in Example 1. For the measurement of thrombin inhibitory activity the homogenates were diluted in enzyme buffer containing 1 pM thrombin. The concentrations of thrombin-like activity or thrombin inhibitory activity were determined from the slopes of the linear part of the dose-response curve.

Brain homogenates from 14 days old wild type or PN-1 knockout mice did not release any measurable amounts of soluble β-galactosidase activity upon incubation with immobilized GPAR1. An excess of thrombin inhibitory activity became apparent when the brain homogenates were assayed in the presence of 1 pM thrombin. In fact a reduction of the β-galactosidase release was detected in the presence of the brain homogenate. The amount of thrombin inhibitor present in the brain homogenates was calculated from these curves. The highest concentration of inhibitor was 817±122 pM, present in the homogenate of the wild type brain, while the thrombin inhibitory activity was reduced to 79±8 pM in the PN-1 knockout brain, equivalent to 9.7% of the wild type level. In the brain of the heterozygous PN-1 knockout mouse, an intermediate concentration of 487±65 pM thrombin inhibitory activity was found. The detected inhibitor is most likely PN-1, due to the reduced level that was found in the brains of the heterozygous mice. However, even in the homogenate from the homozygous PN-1 knockout mouse, thrombin inhibitory activity was evidently measurable, indicating the presence of an inhibitor distinct from PN-1.

In summary, the precise and sensitive measurement of PAR-specific protease activity and protease inhibitory activity in tissue samples is afforded by the present method. The targeted disruption of the PN-1 gene leads to a strong reduction, but not to abolishment of the thrombin inhibitory activity in brain homogenates, thus demonstrating the presence of a second thrombin inhibitor. The reduction in inhibitory activity was measurable using the thrombin substrate S2238, but was confirmed at a more sensitive level using the present assay. No thrombin-like activity, allowing the identification of a putative target protease for PN-1, was detectable in those knockout animals.

Example 9

Measurement of Protease Activity and Protease Inhibitory Activity in Fluids from the Male Murine Reproductive System After the generation of PN-1 knockout mice, the subsequent breeding of the mutant mouse line indicated that many homozygous PN-1 knockout males were sterile. Since PN-1 is expressed at high levels in an androgen dependent fashion in the male reproductive system of wild type mice (Mansuy et al., 1993; Vassalli et al., 1993), its absence may have severe consequences for the fertility of the animal. Possible targets for PN-1 are the serine proteases uPA and plasmin, which can be generated by uPA from plasminogen. We analysed 14 days old PN-1 knockout mice back-crossed into the C57/B16 mouse line described in Example 8.

Collection of Fluids from the Male Reproductive System of mice

Two pairs of adult back-crossed PN-1 knockout mice were anaesthetized and killed by decapitation. The seminal vesicle, the coagulating gland and the vas deferens/cauda epididymis were dissected out and their content was pushed with forceps into eppendorf tubes and mixed with 100 µl enzyme buffer 1×EB$_T$ [50 mM Tris/HCl, pH 8.0, 100 mM NaCl, 0.1% PEG 6000, 0.02% Tween 20]. The samples were stored frozen at −80° C. until use.

Protein Determination

Protein determination of serial dilutions of the fluid samples was carried out using a Bradford-type protein determination kit from BioRad according to the manufacturer's recommendations (Bradford, 1976).

Measurement of the Protease and Protease Inhibitory Activity

The fluids were serially diluted in enzyme buffer with dilutions ranging from 1/200 to 1/600,000. The diluted samples were assayed in triplicates for the presence of thrombin-like activity under the conditions described in Example 1, as well as for thrombin inhibitory activity as described in Example 7. Alternatively, the assay was performed in the presence of 10 pM trypsin. The concentrations of thrombin-like activity or thrombin inhibitory activity were determined from the slopes of the linear part of the dose-response curves.

All examined fluids contained either a measurable amount of proteolytic activity or of thrombin inhibitory activity. The seminal vesicle contains an excess of thrombin inhibitory activity of about 240 fmol per mg protein, which is reduced to 19% in the PN-1 knockout mouse. In the coagulating gland of the wild type mouse a thrombin inhibitory activity is present at a concentration of approximately 10 fmol per mg of protein. In the mutant mouse which is unable to synthesize PN-1, the thrombin inhibitory activity is abolished, thereby unmasking an excess of protease activity. The fluid from the vas deferens displayed a protease activity of about 400 fmol per mg protein, which was increased by 150% in the PN-1 knockout mouse. For one wild type mouse the measurement was performed in the presence of 10 pM trypsin, showing that the inhibitory activity in the seminal vesicle and in the coagulating gland was also able to inhibit trypsin. The sensitive assay described herein has allowed the detection of thrombin and trypsin-like proteases and their inhibitors in fluids from the reproductive system of PN-1 knockout and wild type mice.

In summary, an excess of thrombin inhibitory activity was detected in the coagulating gland of wild type mice, which was absent in the PN-1 knockout mice, resulting in an excess of an unidentified thrombin-like protease activity. A second thrombin inhibitory activity was detected in the seminal vesicle. In the vas deferens and cauda epididymis, the disruption of the PN-1 gene leads to an increase of an unidentified protease activity that was also present in the wild type mouse at lower levels. Thus, the methods of the present invention can be used to detect hitherto unidentified proteases and protease inhibitors that provide further biological targets for PAR regulation.

Example 10

Analysis of Soluble or Cell Surface Associated Proteases

This example describes the preparation of a fusion protein expressed in a membrane-bound fashion on the surface of mammalian cells in culture, thereby allowing the analysis of soluble or cell surface associated proteases. Using this format, we have been able to demonstrate thrombin-mediated release of a reporter enzyme into the medium of cultured cells. The cultured mouse neuroblastoma cells (Nb2a or Cho-E cells) were transfected with the cDNA of a membrane-anchored fusion protein of human placental alkaline phosphatase and the extracellular and first transmembrane domains of PAR1.

Signal intensities can be easily optimized for each PAR fusion construct, for example, by selection of a cell line that allows high expression levels and by creating a cell line stably expressing the receptor fusion protein. The cell based format of the assay can be used for the sensitive detection of proteases that are able to activate proenzymes, such as prothrombin, or to cleave and release the reporter enzyme directly.

As is apparent to one of ordinary skill in the art, the above Examples can be easily modified to include the use of various reporter molecules or PAR sequences to detect PAR activators, inactivators, agonists and antagonists in samples from various origins. In addition, the PAR fusion proteins described herein are useful to screen for any PAR binding protein or molecule, which can then be identified by methods known in the art (e.g., proteomics).

TABLE 1

GPAR assays: β-Galactosidase release rates by potential activators and inactivators of PARs

| | Potential Activators | | | | | | Potential Inactivators | |
|---|---|---|---|---|---|---|---|---|
| | Thrombin | Trypsin | act. Protein C | Plasmin | Urokinase | tPA | Elastase | Chymotrypsin |
| GPAR1 | $2.6 * 10^3$ | $9.7 * 10^1$ | $\leq 1 * 10^{-2}$ [a] | $4.1 * 10^0$ | $\leq 1 * 10^{-2}$ | $\leq 1 * 10^{-2}$ | $7.8 * 10^1$ | $5.8 * 10^1$ |
| GPAR1$^{R45S}$ | $7 * 10^{-2}$ | $3.4 * 10^1$ | $\leq 1 * 10^{-2}$ | $2.9 * 10^{-1}$ | $\leq 1 * 10^{-2}$ | $\leq 1 * 10^{-2}$ | $1.4 * 10^2$ | $7.8 * 10^1$ |
| GPAR2 | $1 * 10^{-2}$ | $3.7 * 10^2$ | $\leq 1 * 10^{-2}$ | $6.7 * 10^{-1}$ | $\leq 1 * 10^{-2}$ | $\leq 1 * 10^{-2}$ | $2.4 * 10^1$ | $5.6 * 10^0$ |
| GPAR2$^{R34S}$ | $\leq 1 * 10^{-2}$ | $4.2 * 10^1$ | $\leq 1 * 10^{-2}$ | $3.5 * 10^{-1}$ | $\leq 1 * 10^{-2}$ | $\leq 1 * 10^{-2}$ | $1.6 * 10^1$ | $4.3 * 10^0$ |
| GPAR3 | $4.1 * 10^2$ | $3.6 * 10^1$ | $\leq 1 * 10^{-2}$ [a] | $3.4 * 10^{-1}$ | $\leq 1 * 10^{-2}$ | $3 * 10^{-2}$ | $5.0 * 10^1$ | $4.7 * 10^0$ |
| GPAR3$^{R37S}$ | $3.4 * 10^0$ | $3.0 * 10^1$ | $\leq 1 * 10^{-2}$ | $1.6 * 10^{-1}$ | $\leq 1 * 10^{-2}$ | $\leq 1 * 10^{-2}$ | $9.3 * 10^1$ | $4.5 * 10^0$ |
| GPAR4 | $4.3 * 10^0$ | $1.5 * 10^1$ | $\leq 1 * 10^{-2}$ | $4.8 * 10^{-1}$ | $\leq 1 * 10^{-2}$ | $\leq 1 * 10^{-2}$ | $1.2 * 10^1$ | $3.4 * 10^0$ |
| GPAR4$^{R47S}$ | $2 * 10^{-2}$ | $7.8 * 10^0$ | $\leq 1 * 10^{-2}$ | $2.6 * 10^{-1}$ | $\leq 1 * 10^{-2}$ | $\leq 1 * 10^{-2}$ | $1.1 * 10^1$ | $8.4 * 10^0$ |

Note. Immobilized GPAR fusion proteins were incubated with the above listed proteases and the release of β-Galactosidase was detected and evaluated as described. The data represent the average of at least two experiments with triplicate determinations. All values are in mmol $_{\beta\text{-Galactosidase}}$/(mol$_{Protease}$ * min).
[a] Determined in the presence of hirudin

---

What is claimed is:

1. A method of identifying a PAR cleaving molecule, said method comprising the steps of:
   (a) providing an immobilized PAR cleavage peptide linked to a reporter molecule;
   (b) contacting said immobilized PAR cleavage peptide with a candidate PAR cleaving molecule; and
   (c) detecting release of said reporter molecule, wherein said detection identifies the candidate PAR cleaving molecule as a PAR cleaving molecule.

2. The method of claim 1, wherein said PAR cleavage peptide comprises residues 38 to 41 of EMBL Accession No. L03529 (SEQ ID NO:19), residues 35 to 38 of EMBL Accession No. Z48043 (SEQ ID NO:21), residues 34 to 37 of EMBL Accession No. U92972 (SEQ ID NO:22), or residues 44 to 47 of EMBL Accession No. AF055917 (SEQ ID NO:23).

3. The method of claim 1, wherein said PAR cleavage peptide is linked to a biotin moiety and is immobilized via a biotin-avidin or biotin-streptavidin interaction.

4. The method of claim 1, further comprising determining the cleavage site of said PAR cleavage peptide by said PAR cleaving molecule.

5. The method of claim 4, wherein said PAR cleaving molecule is identified as being a PAR activator if said cleavage site is at a biological cleavage site.

6. The method of claim 4, wherein said PAR cleaving molecule is identified as a PAR inactivator if said cleavage site is not at a biological cleavage site.

7. The method of claim 1, further comprising contacting said immobilized PAR cleavage peptide with a potential PAR modulator and determining a change in the level of released reporter molecule as compared to when said PAR modulator is absent.

8. A kit for identifying a PAR cleaving molecule, comprising a PAR fusion protein and instructions for use in a method for identifying a PAR cleaving molecule.

9. The method of claim 1, wherein said PAR cleavage peptide further comprises an amino acid sequence of a PAR extracellular domain.

10. The method of claim 1, wherein said PAR cleavage peptide further comprises the amino acid sequence GDE.

11. The method of claim 1, wherein said reporter molecule is a reporter enzyme.

12. The method of claim 11, wherein said reporter enzyme is selected from the group consisting of beta-galactosidase, glucosidases, chloramphenicol acetyltransferase, glucoronidases, luciferase, peroxidases, phosphatases, oxidoreductases, dehydrogenases, transferases, isomerases, kinases, reductases, deaminases, catalases and urease.

13. The method of claim 12, wherein said reporter enzyme is beta-galactosidase.

14. The method of claim 1, wherein said PAR cleavage peptide is linked to a pair of interacting reporter molecules.

15. The method of claim 14, wherein said interacting reporter molecules are selected from the group consisting of cyan fluorescent protein and yellow fluorescent protein, yellow fluorescent protein and red fluorescent protein, aequorin and GFP and luciferase and YFP.

16. The kit of claim 8, wherein said PAR fusion protein is a PAR beta-galactosidase fusion protein.

* * * * *

SEQUENCE LISTING

<160> NUMBER OF SEQ ID NOS: 18

<210> SEQ ID NO 1
<211> LENGTH: 46
<212> TYPE: DNA
<213> ORGANISM: mus

<400> SEQUENCE: 1
cacacagcgg ccgcgtcgac gatgagcgaa aaatacatcg tcacct          46

<210> SEQ ID NO 2
<211> LENGTH: 53
<212> TYPE: DNA
<213> ORGANISM: mus

<400> SEQUENCE: 2
cacacttaat taatctagat ttgtacagtt tttgacacca gaccaactgg taa    53

<210> SEQ ID NO 3
<211> LENGTH: 76
<212> TYPE: DNA
<213> ORGANISM: mus

<400> SEQUENCE: 3
cacacaccat ggggtcgacg atgagcgtgt acagtggagg ttcaggcgga tcaagccagc    60
cagaatcaga gaggac                                                    76

<210> SEQ ID NO 4
<211> LENGTH: 34
<212> TYPE: DNA
<213> ORGANISM: mus

<400> SEQUENCE: 4
gagagaacta gtggggctgg tcagatatcc ggag                         34

<210> SEQ ID NO 5
<211> LENGTH: 136
<212> TYPE: DNA
<213> ORGANISM: mus

```
<400> SEQUENCE: 5
cacacaccat gggactcgag gaggtactag tggaggttca caccatcatc accaccatgc      60
agcggctctg aacgatattt tcgaagctca gaaaatcgaa tggcacgagt agtctagacg     120
tccaggtacc agagag                                                     136

<210> SEQ ID NO 6
<211> LENGTH: 45
<212> TYPE: DNA
<213> ORGANISM: mus

<400> SEQUENCE: 6
cacacatcta gataaggatc catgaaggat aacaccgtgc cactg                      45

<210> SEQ ID NO 7
<211> LENGTH: 41
<212> TYPE: DNA
<213> ORGANISM: mus

<400> SEQUENCE: 7
cacacaggta ccaagcttat ttttctgcac tacgcaggga t                          41

<210> SEQ ID NO 8
<211> LENGTH: 42
<212> TYPE: DNA
<213> ORGANISM: mus

<400> SEQUENCE: 8
ctcatgtaca gtggaggttc aggaggctcg agccagccag aa                         42

<210> SEQ ID NO 9
<211> LENGTH: 114
<212> TYPE: DNA
<213> ORGANISM: mus

<400> SEQUENCE: 9
cacacatgta cagtggaggt tcaggcggct cgagcgagaa ccttgcaccg ggacgcaaca      60
acagtaaagg aagaagtctt attggcagat tagaaaccca gcctccaatc actg           114

<210> SEQ ID NO 10
<211> LENGTH: 112
<212> TYPE: DNA
<213> ORGANISM: mus

<400> SEQUENCE: 10
cacacaacta gtgaccgtgg tcagcttccc ggtgaggatg gacgcagaga actcatcgat      60
ggaaaagcct ggttctaccg gaaccccttt cccagtgatt ggaggctggg tt             112

<210> SEQ ID NO 11
<211> LENGTH: 135
<212> TYPE: DNA
<213> ORGANISM: mus

<400> SEQUENCE: 11
tgtacagtgg aggttcaggc ggctcgagcg gcataaatgt tcagacaac tcagcaaagc       60 caaccttaac tattaagagt tttaatgggg gtccccaaaa tacctttgaa gaattcccac     120
tttctgacat agagg                                                      135

<210> SEQ ID NO 12
```

-continued

```
<211> LENGTH: 134
<212> TYPE: DNA
<213> ORGANISM: human

<400> SEQUENCE: 12
actagtactt aaggaacttc tcaggtatcc tatggtagca ttattcacgt ggagagttga      60
aatactgtcc tcgggacact ccgcttttat agttgtggtg gctcctgtcc agccctctat    120
gtcagaaagt ggga                                                      134

<210> SEQ ID NO 13
<211> LENGTH: 115
<212> TYPE: DNA
<213> ORGANISM: human

<400> SEQUENCE: 13
cacacactcg agcggcggca cccagacccc cagcgtctac gacgagagcg ggagcaccgg     60
aggtggtgat gacagcacgc cctcaatcct gcctgccccc cgcggctacc caggc         115

<210> SEQ ID NO 14
<211> LENGTH: 113
<212> TYPE: DNA
<213> ORGANISM: human
<220> FEATURE:

<400> SEQUENCE: 14
tgtgtgacta gtcctggtgg gcacccagcc cagaagcagt gcccgtgagc tgtccggaag     60
ctccagggtg tcactgtcat tggcacagac ttggcctggg tagccgcggg ggg           113

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: mouse
      sequence flanked by unrelated sequences

<400> SEQUENCE: 15

Gly Gly Ser Gly Gly Ser Ser Gln Pro Glu Ser Glu Arg Thr Asp Ala
  1               5                  10                  15

Thr Val Asn Pro Arg Ser Phe Phe Leu Arg Asn Pro Ser Glu Asn Thr
                 20                  25                  30

Phe Glu Leu Val Pro Leu Gly Asp Glu Glu Glu Glu Lys Asn Glu
             35                  40                  45

Ser Val Leu Leu Glu Gly Arg Ala Val Tyr Leu Asn Ile Ser Leu Pro
     50                  55                  60

Pro His Thr Pro Pro Pro Phe Ile Ser Glu Asp Ala Ser Gly Tyr
 65                  70                  75                  80

Leu Thr Ser Pro Thr Ser Gly Gly Ser His His His His His Gly
                 85                  90                  95

Gly Ser Leu Asn Asp Ile Phe Glu Ala Gln Lys Phe Glu Trp His Glu
            100                 105                 110

<210> SEQ ID NO 16
<211> LENGTH: 87
<212> TYPE: PRT
<213> ORGANISM: Artificial Sequence
<220> FEATURE:
<223> OTHER INFORMATION: Description of Artificial Sequence: mouse
      sequence flanked by unrelated sequences

<400> SEQUENCE: 16
```

-continued

Gly Gly Ser Gly Gly Ser Glu Asn Leu Ala Pro Gly Arg Asn Asn Ser
1               5                   10                  15

Lys Gly Arg Ser Leu Ile Gly Arg Leu Glu Thr Gln Pro Pro Ile Thr
            20                  25                  30

Gly Lys Gly Val Pro Val Glu Pro Gly Phe Ser Ile Asp Glu Phe Ser
        35                  40                  45

Ala Ser Ile Leu Thr Gly Lys Leu Thr Thr Val Thr Ser Gly Gly Ser
    50                  55                  60

His His His His His Gly Gly Ser Leu Asn Asp Ile Phe Glu Ala
65                  70                  75                  80

Gln Lys Phe Glu Trp His Glu
                85

<210> SEQ ID NO 17
<211> LENGTH: 106
<212> TYPE: PRT
<213> ORGANISM: Artificial Sequence
<220> FEATURE:
<223> OTHER INFORMATION: Description of Artificial: mouse sequence
      flanked by unrelated sequences

<400> SEQUENCE: 17

Gly Gly Ser Gly Gly Ser Ser Gly Ile Asn Val Ser Asp Asn Ser Ala
1               5                   10                  15

Lys Pro Thr Leu Thr Ile Lys Ser Phe Asn Gly Gly Pro Gln Asn Thr
            20                  25                  30

Phe Glu Glu Phe Pro Leu Ser Asp Ile Glu Gly Trp Thr Gly Ala Thr
        35                  40                  45

Thr Thr Ile Lys Ala Glu Cys Pro Glu Asp Ser Ile Ser Thr Leu His
    50                  55                  60

Val Asn Asn Ala Thr Ile Gly Tyr Leu Arg Ser Ser Leu Ser Thr Ser
65                  70                  75                  80

Gly Gly Ser His His His His His Gly Gly Ser Leu Asn Asp Ile
                85                  90                  95

Phe Glu Ala Gln Lys Phe Glu Trp His Glu
            100                 105

<210> SEQ ID NO 18
<211> LENGTH: 96
<212> TYPE: PRT
<213> ORGANISM: Artificial Sequence
<220> FEATURE:
<223> OTHER INFORMATION: Description of Artificial Sequence:human
      sequence flanked by unrelated sequences

<400> SEQUENCE: 18

Gly Gly Ser Gly Gly Ser Ser Gly Gly Thr Gln Thr Pro Ser Val Tyr
1               5                   10                  15

Asp Glu Ser Gly Ser Thr Gly Gly Asp Asp Ser Thr Pro Ser Ile
            20                  25                  30

Leu Pro Ala Pro Arg Gly Tyr Pro Gly Gln Val Cys Ala Asn Asp Ser
        35                  40                  45

Asp Thr Leu Glu Leu Pro Asp Ser Ser Arg Ala Leu Leu Leu Gly Trp
    50                  55                  60

```
Val Pro Thr Arg Thr Ser Gly Gly Ser His His His His His Gly
 65              70              75              80

Gly Ser Leu Asn Asp Ile Phe Glu Ala Gln Lys Phe Glu Trp His Glu
             85              90              95
```